US009623122B2

(12) United States Patent
Hara et al.

(10) Patent No.: US 9,623,122 B2
(45) Date of Patent: Apr. 18, 2017

(54) MOLECULAR ASSEMBLY USING BRANCHED AMPHIPHILIC BLOCK POLYMER, AND DRUG TRANSPORTATION SYSTEM

(71) Applicants: SHIMADZU CORPORATION, Kyoto-shi, Kyoto (JP); KYOTO UNIVERSITY, Kyoto-shi, Kyoto (JP)

(72) Inventors: Isao Hara, Kyoto (JP); Eiichi Ozeki, Kyoto (JP); Shunsaku Kimura, Kyoto (JP); Akira Makino, Kyoto (JP)

(73) Assignees: SHIMADZU CORPORATION, Kyoto (JP); KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 14/425,429

(22) PCT Filed: Sep. 3, 2013

(86) PCT No.: PCT/JP2013/073707
§ 371 (c)(1),
(2) Date: Mar. 3, 2015

(87) PCT Pub. No.: WO2014/038558
PCT Pub. Date: Mar. 13, 2014

(65) Prior Publication Data
US 2015/0202327 A1    Jul. 23, 2015

(30) Foreign Application Priority Data

Sep. 4, 2012    (JP) ................. 2012-194624

(51) Int. Cl.
*A61K 31/74* (2006.01)
*A61K 49/00* (2006.01)
*A61K 9/51* (2006.01)
A61K 47/48 (2006.01)
A61K 51/04 (2006.01)
A61K 49/12 (2006.01)
A61K 51/06 (2006.01)

(52) U.S. Cl.
CPC ........ *A61K 49/0054* (2013.01); *A61K 9/5153* (2013.01); *A61K 47/482* (2013.01); *A61K 49/0034* (2013.01); *A61K 49/0089* (2013.01); A61K 47/48 (2013.01); A61K 47/48007 (2013.01); A61K 49/12 (2013.01); A61K 49/124 (2013.01); A61K 51/0404 (2013.01); A61K 51/06 (2013.01)

(58) Field of Classification Search
None
See application file for complete search history.

(56) References Cited

U.S. PATENT DOCUMENTS

| 2006/0275775 | A1* | 12/2006 | Weissleder | A61B 5/0071 435/6.12 |
|---|---|---|---|---|
| 2007/0160561 | A1* | 7/2007 | Ouali | C08F 293/00 424/70.16 |
| 2008/0019908 | A1 | 1/2008 | Akitsu et al. | |
| 2011/0104056 | A1 | 5/2011 | Hara et al. | |
| 2013/0149252 | A1 | 6/2013 | Hara et al. | |
| 2014/0127132 | A1 | 5/2014 | Ozeki et al. | |
| 2015/0031988 | A1 | 1/2015 | Takeuchi et al. | |

FOREIGN PATENT DOCUMENTS

| EP | 1 780 234 A1 | 5/2007 |
|---|---|---|
| EP | 2 305 214 A1 | 4/2011 |
| EP | 2 725 053 A1 | 4/2014 |
| EP | 2 745 850 A1 | 6/2014 |
| JP | 2008-24816 A | 2/2008 |
| WO | WO-2009/148121 A1 | 12/2009 |
| WO | WO 2012/026316 A1 | 3/2012 |
| WO | WO-2012/128326 A1 | 9/2012 |
| WO | WO-2012/176885 A1 | 12/2012 |
| WO | WO-2013/039111 A1 | 3/2013 |

OTHER PUBLICATIONS

International Search Report for Application No. PCT/JP2013/073707 mailed Nov. 5, 2013.
Makino, Akira et al., "Near-infrared fluorescence tumor imaging using nanocarrier composed of poly(L-lactic acid)-block-poly(sarcosine) amphiphilic polydesipeptide", Biomaterials, 2009, vol. 30, pp. 5156-5160.
Makino, Akira at al., "Control of in vivo blood clearance time of polymeric micelle by stereochemistry of amphiphilic polydepsipeptides", Journal of Controlled Release, 2012, vol. 161, No. 3, pp. 821-825.
Koide: Hiroyuki et al., "Eluddation of Accelerated Blood Clearance Phenomenon Caused by Repeat Injection of PEGylated Nanocarriers", Yakugaku Zasshi, 2009, vol. 129, No. 12, pp. 1445-1451.

(Continued)

Primary Examiner — James Rogers
(74) Attorney, Agent, or Firm — Cheng Law Group, PLLC

(57) ABSTRACT

The present invention provides a molecular assembly whose retention time in a target site is adjusted depending on the kind or purpose of a labeling agent or drug encapsulated therein, and a molecular assembly that can suppress the ABC phenomenon and that can be administered more than once within a short span. A molecular assembly comprising: a branched-type amphiphilic block polymer A comprising a branched hydrophilic block comprising sarcosine and a hydrophobic block comprising a polylactic acid chain; and a functional substance F comprising a functional site and a polylactic acid chain, wherein the polylactic acid chain constituting the hydrophobic block of the amphiphilic block polymer A comprises L-lactic acid units, and the polylactic acid chain contained in the functional substance F comprises D-lactic acid units, or the polylactic acid chain constituting the hydrophobic block of the amphiphilic block polymer A comprises D-lactic acid units, and the polylactic acid chain contained in the functional substance F comprises L-lactic acid units.

13 Claims, 8 Drawing Sheets

(56) References Cited

OTHER PUBLICATIONS

Makino, Akira at al., "Effect of poly(lactic acid)-stereochemistry on tumor imaging with using nanocarrier Lactosome", Abstracts of the 2012 World Molecular Imaging Congress.

Makino, Akira at al., "Small particulation of polymeric micelle, "Lactosome", and its effect on ABC phenomenon relief", Polymer Preprints, 2011, Vol, 60, No. 2, pp. 5026-5027.

Makino, Akira at at "Evasion from the accelerated blood clearance (ABC) phenomenon of "Lactosome" by micelle size control", Molecular Imaging and Biology, 2012, vol. 14, Suppl. 1, S67, P069.

Ham, Eri, "Pharmacokinetic change of nanoparticulate formulation 'Lactosome' on multiple administrations", International Immunopharmacology, 2012, vol. 14, No. 3, pp. 261-266.

Ozeki, Eiichi et al., "Development of Molecular Probe with Using nanocarrier, 'Lactosome', Composed of Amphiphilic Polydepsipeptide, Poly(L-lactic acid) and Poly(sarcosine) ", Shimadzu Review, 2009, vol. 66, pp. 3-12.

Supplementary European Search Report for the Application No. EP 13 83 6159 dated Mar. 23, 2016.

Written Opinion of the International Searching Authority (PCT/ISA/237) for Application No. PCT/JP2013/073707 mailed Nov. 5, 2013 (English Translation mailed Mar. 19, 2015).

\* cited by examiner

MOLECULAR ASSEMBLY USING BRANCHED AMPHIPHILIC BLOCK POLYMER, AND DRUG TRANSPORTATION SYSTEM

TECHNICAL FIELD

The present invention belongs to the fields of supramolecular chemistry, collaborative region of medicine, engineering and pharmacy, and nanomedicine. The present invention relates to a nano-carrier as a molecular probe fox molecular imaging, a nano-carrier for drug delivery, and a dispersing agent for hydrophobic compounds. More specifically, the present invention relates to a molecular assembly using branched-type amphiphilic block polymer, and a drug delivery system.

BACKGROUND ART

WO 2009/148121 (Patent Document 1) and Biomaterials, 2009, Vol. 30, p. 5156-5160 (Non-Patent Document 1) disclose that an amphiphilic block polymer having a polylactic acid chain as a hydrophobic block and a polysarcosine chain as a hydrophilic block self-assembles in an aqueous solution to form a polymeric micelle (lactosome) having a particle size of 30 nm or more. It is known that the lactosomes exhibit high retentivity in blood and the amount of the lactosomes accumulated in the liver is significantly reduced as compared to polymeric micelles that have been already developed. The lactosomes utilize the property that nanoparticles with a particle size of several tens of nanometers to several hundreds of nanometers retained in blood are likely to be accumulated in cancer (Enhanced Permeation and Retention (EPR) effect), and therefore can be used as nano-carriers for cancer site-targeting molecular imaging or drug delivery.

Journal of Controlled Release, Volume 161, Issue 3, 10 Aug. 2012, Pages 821-825 (Non-Patent Document 2) discloses three kinds of lactosomes prepared by, respectively, encapsulating three kinds of ICG (indocyanine green)-labeled polylactic acids different in stereochemistry (ICG-PLLA, ICG-PDLA, ICG-PDLLA) in the polymeric micelle (lactosome) composed of a linear type amphiphilic block polymer having a poly-L-lactic acid (PLLA) chain as an above-mentioned hydrophobic block and a polysarcosine chain as an above-mentioned hydrophilic block, and also discloses the influence of the stereochemistry of the ICG-labeled polylactic acid on the behavior of the lactosome in vivo. These lactosomes have a particle diameter of 35 nm or more.

A phenomenon, namely "Accelerated Blood Clearance (ABC) phenomenon" is known, in which an immune system is activated by administering polymeric micelles composed of a synthetic polymer to a living body once so that when the same polymeric micelles are administered again, they are accumulated in the liver due to the action of the immune system. Details of the mechanism of development of this ABC phenomenon are more or less clarified. YAKUGAKU ZASSHI, 2009, Vol. 129, No. 12, p. 1445-1451 (Non-Patent Document 3) reports that the development of the ABC phenomenon is suppressed when polymeric micelles having a particle size of 30 nm or less are used.

PRIOR ART DOCUMENTS

Patent Document

Patent Document 1: WO 2009/148121

Non-Patent Documents

Non-Patent Document 1: Biomaterials, 2009, Vol. 30, p. 5156-5160
Non-Patent Document 2: Journal of Controlled Release, Volume 161, Issue 3, 10 Aug. 2012, Pages 821-825
Non-Patent Document 3: YAKUGAKU ZASSHI, 2009, Vol. 129, No. 12, p. 1445-1451

SUMMARY OF THE INVENTION

Problems to be Solved by the Invention

As described above, the lactosome disclosed in Patent Document 1 and Non-Patent Documents 1 and 2 has high retentivity in blood, and the amount of the lactosome accumulated in the liver is significantly reduced as compared to polymeric micelles that have already been developed. Further, the lactosome can be used as a nano-carrier for tumor- or inflamed site-targeted molecular imaging or drug delivery due to its EPR effect.

However, the above-mentioned lactosome has a particle diameter of 30 nm or more. From the viewpoint of delivery circulation into thinner capillary blood vessels, entry into a diseased site, such as a small cancer, via capillary blood vessels, and higher EPR effect, a molecular assembly having a smaller particle diameter is expected to be developed.

Depending on the kind or purpose of a labeling agent (signal agent) or drug encapsulated in a molecular assembly, in some cases, the molecular assembly is expected to be excreted in a relatively short time after delivery to a target site, while in other cases, the molecular assembly is expected to be retained in a target site for a long time.

Further, also in the case of the lactosomes (as in the case of polymeric micelles composed of a synthetic polymer), the ABC phenomenon occurs. Therefore, there is a problem that the lactosomes cannot be administered more than once while an immunological memory effect is reduced.

Therefore, an object of the present invention is to provide a molecular assembly (polymeric micelle pharmaceutical preparation) whose retention time in a target site is adjusted depending on the kind or purpose of a labeling agent or drug encapsulated therein. Further, an object of the present invention is to provide a molecular assembly (polymeric micelle pharmaceutical preparation) that can suppress the ABC phenomenon and that can be administered more than once within a short span.

Means for Solving the Problems

The present inventors have intensively studied, and as a result, have found that the above objects of the present invention can be achieved by molecularly designing an amphiphilic block polymer so that its hydrophilic block has a branched structure constituted from a plurality of sarcosine chains, and in addition, lactic acid units in a polylactic acid chain constituting a hydrophobic block of the amphiphilic block polymer and lactic acid units in a labeling agent- and/or drug-containing polylactic acid chain to be encapsulated in a molecular assembly have a specific stereochemistry, which has led to the completion of the present invention.

The present invention includes the followings.

(1) A molecular assembly comprising:
    a branched-type amphiphilic block polymer A comprising
        a branched hydrophilic block comprising sarcosine and
        a hydrophobic block comprising a polylactic acid chain; and a functional substance F comprising a functional site and a polylactic acid chain, wherein the polylactic acid chain constituting the hydrophobic block of the amphiphilic block polymer A comprises L-lactic acid units, and the polylactic acid chain contained in the functional substance F comprises D-lactic acid units, or the polylactic acid chain constituting the hydrophobic block of the amphiphilic block polymer A comprises D-lactic acid units, and the polylactic acid chain contained in the functional substance F comprises L-lactic acid units.

When the stereochemistry of the polylactic acid chain (A-PLA) constituting the hydrophobic block of the amphiphilic block polymer A and the stereochemistry of the polylactic acid chain (F-PLA) contained in the functional substance F are made different from each other, the retention time of the molecular assembly in a target site can be prolonged.

(2) The molecular assembly according to (1), wherein the hydrophilic block comprises 2 to 200 sarcosine units in total.
(3) The molecular assembly according to (1) or (2), wherein the number of branches of the hydrophilic block is 3.
(4) The molecular assembly according to any one of (1) to (3), wherein the polylactic acid chain constituting the hydrophobic block comprises 10 to 400 lactic acid units.
(5) The molecular assembly according to any one of (1) to (4), wherein the hydrophobic block is not branched.
(6) The molecular assembly according to (5), wherein the plurality of hydrophilic blocks extend as branches from one carbon atom in a molecular chain containing the polylactic acid chain of the hydrophobic block.
(7) The molecular assembly according to (6), wherein the amphiphilic block polymer A has a structure represented by the following formula (I):

[Chemical formula 1]

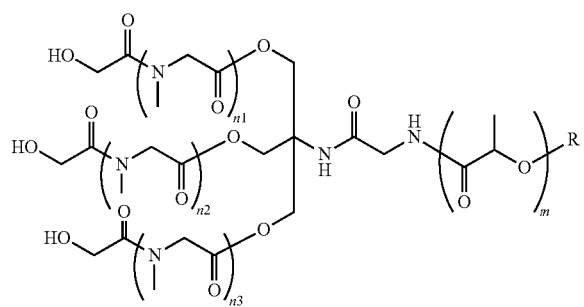

(I)

wherein n1, n2, and n3 represent numbers whose sum is 3 to 200, m represents a number of 15 to 60, and R represents a hydrogen atom or an organic group.
(8) The molecular assembly according to any one of (1) to (7), wherein in the amphiphilic block polymer A, a ratio of a total number of the sarcosine units contained in the hydrophilic block to a total number of the lactic acid units contained in the hydrophobic block is 0.05 or more and less than 1.8.
(9) The molecular assembly according to any one of (1) to (8), wherein the functional site of the functional substance F is a site selected from the group consisting of a signal agent and a drug.
(10) The molecular assembly according to any one of (1) to (9), wherein the functional substance F is contained in an amount of 20 mol % or less with respect to the amphiphilic block polymer A.

(11) The molecular assembly according to any one of (1) to (10), whose particle diameter is 10 to 30 nm.
(12) The molecular assembly according to any one of (1) to (11), which is obtained by a preparation method comprising the steps of:

preparing a solution, in a container, containing the branched-type amphiphilic block polymer A and the functional substance F in an organic solvent;

removing the organic solvent from the solution to obtain a film comprising the branched-type amphiphilic block polymer A and the functional substance F on an inner wall of the container; and adding water or an aqueous solution into the container and performing ultrasonic treatment to convert the film into a molecular assembly, thereby obtaining a dispersion liquid of the molecular assembly.

(13) The molecular assembly according to any one of (1) to (11), which is obtained by a preparation method comprising the steps of:

preparing a solution, in a container, containing the branched-type amphiphilic block polymer A and the functional substance F in an organic solvent;

dispersing the solution into water or an aqueous solution; and removing the organic solvent.

(14) A drug delivery system comprising administering the molecular assembly according to any one of (1) to (13) as a molecular probe to a non-human animal.
(15) A molecular assembly comprising:

a branched-type amphiphilic block polymer A comprising a branched hydrophilic block comprising sarcosine and a hydrophobic block comprising a polylactic acid chain; and a functional substance F comprising a functional site and a polylactic acid chain, wherein the polylactic acid chain constituting the hydrophobic block of the amphiphilic block polymer A comprises L-lactic acid units, and the polylactic acid chain contained in the functional substance F comprises DL-lactic acid units, or the polylactic acid chain constituting the hydrophobic block of the amphiphilic block polymer A comprises D-lactic acid units, and the polylactic acid chain contained in the functional substance F comprises DL-lactic acid units.

When the polylactic acid chain (F-PLA) contained in the functional substance F comprises DL-lactic acid units in contrast to the stereochemistry of the polylactic acid chain (A-PLA) constituting the hydrophobic block of the amphiphilic block polymer A, the retention time of the molecular assembly in a target site is shortened so that the molecular assembly is quickly excreted to the outside of the body.

The item according to any one of (2) to (13) is applied also to the molecular assembly according to (15). Further, the drug delivery system according to (14) is also applied to the molecular assembly according to (15).

Effects of the Invention

According to the present invention, the branched structure of the hydrophilic block makes it possible to provide a molecular assembly (i.e., a polymeric micelle; lactosome) having a small particle diameter (e.g., a particle diameter less than 30 nm) that conventional lactosomes cannot have. The molecular assembly according to the present invention has a small particle diameter, and therefore can easily be circulated also into thinner capillary blood vessels, can more easily enter a diseased site such as a small cancer via capillary blood vessels, and can more quickly accumulate in a cancer site due to its higher EPR effect.

When the stereochemistry of the polylactic acid chain (referred to as "A-PLA") constituting the hydrophobic block of the amphiphilic block polymer A and the stereochemistry of the polylactic acid chain (referred to as "F-PLA") contained in the functional substance F are made different from each other, the labeling agent (signal agent) or drug encapsulated in the molecular assembly can be retained in a target cancer site for a long time after delivery to the target site. The reason for this is considered to be because the polylactic acid chain (A-PLA) and the polylactic acid chain (F-PLA) form a stereocomplex with each other so that the molecular assembly maintains its stability despite its small particle diameter. Further, it is considered that the helix structure of the polylactic acid chain (A-PLA) and the helix structure of the polylactic acid chain (F-PLA) are different from each other, and the hydrophobic functional site bound to the polylactic acid chain (F-PLA) is easily retained in the hydrophobic inside of the molecular assembly having a core/shell structure so that the stability of the molecular assembly is further improved.

On the other hand, when the polylactic acid chain (referred to as "F-PLA") contained in the functional substance F comprises DL-lactic acid units in contrast to the stereochemistry of the polylactic acid chain (A-PLA) constituting the hydrophobic block of the amphiphilic block polymer A, the retention time of the molecular assembly in a target site is shortened so that the molecular assembly is quickly excreted to the outside of the body. The reason for this may be considered to be because the above-described stereocomplex formation does not occur between the polylactic acid chain (A-PLA) and the polylactic acid chain (F-PLA) so that the effect of stereocomplex formation on the stabilization of the molecular assembly cannot be obtained. Further, it is considered that the hydrophobic functional site bound to the polylactic acid chain (F-PLA) is less likely to be retained in the hydrophobic inside of the molecular assembly having a core/shell structure.

Further, according to the molecular assembly of the present invention, even in any cases of the stereochemistry, the distribution of the molecular assembly in thinner capillary blood vessels is accelerated and therefore the molecular assembly is distributed throughout the body, which makes it possible to reduce background signals. That is, it is possible to increase the ratio of contrast at tumor site to background contrast. This makes it possible to achieve short-time imaging.

Further, according to the molecular assembly of the present invention, the molecular assembly has a dense polymer brush structure of sarcosine chains in its surface due to the branched structure of the hydrophilic block. Therefore, the development of the ABC phenomenon can be suppressed irrespective of whether or not the particle diameter of the molecular assembly is less than 30 nm.

According to the present invention, there is provided a molecular assembly (polymeric micelle pharmaceutical preparation) whose retention time in a target site is adjusted depending on the kind or purpose of a labeling agent or drug to be encapsulated therein. Further, there is provided a molecular assembly (polymeric micelle pharmaceutical preparation) that can suppress the ABC phenomenon and that can be administered more than once within a short span.

MODE FOR CARRYING OUT THE INVENTION

[1. Branched-Type Amphiphilic Block Polymer A]

Figure 1:
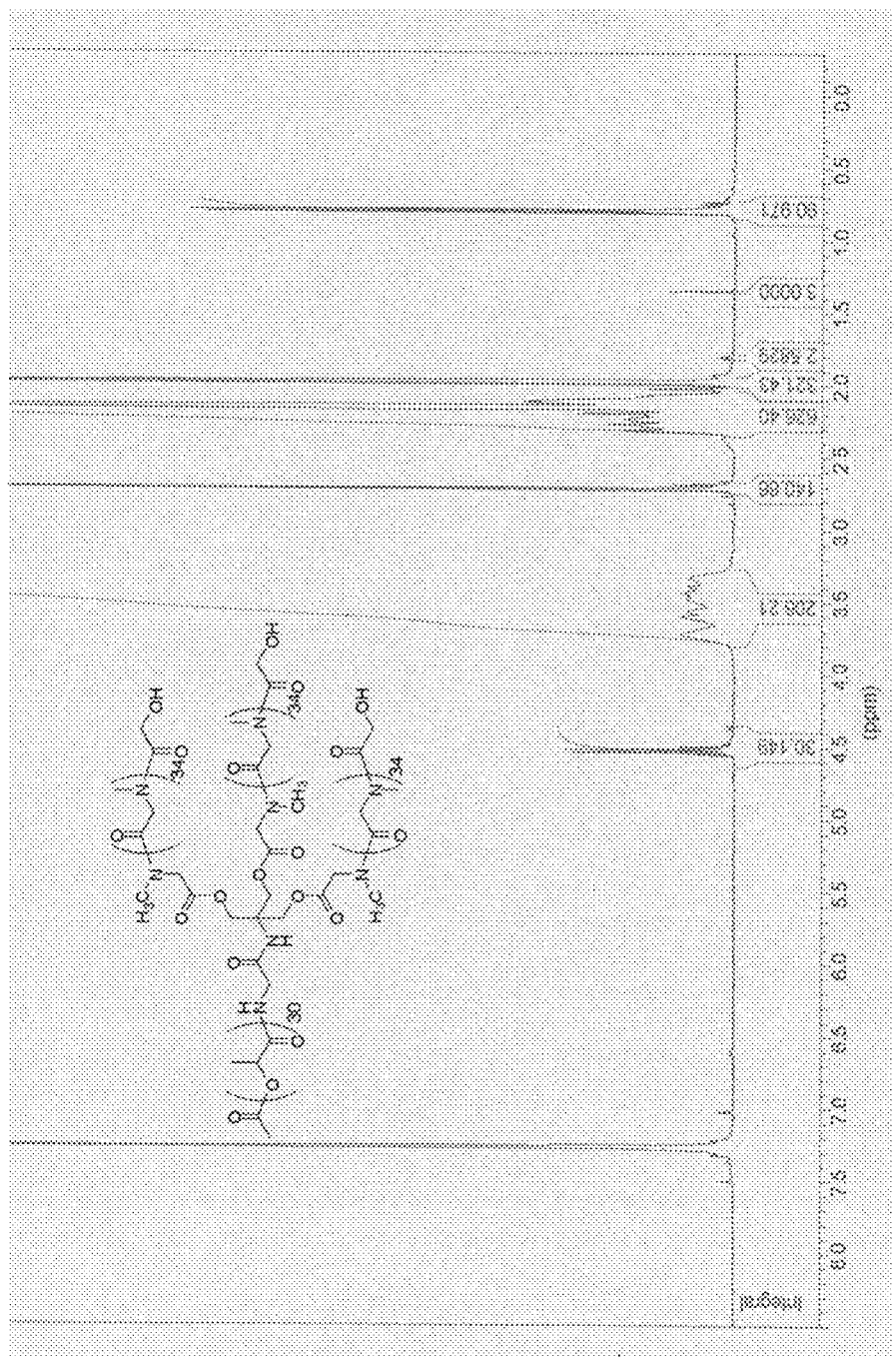
FIG. 1 is a 1H NMR spectrum of a branched-type amphiphilic block polymer synthesized in Synthesis Example 1.

An amphiphilic block polymer A according to the present invention comprises a branched hydrophilic block comprising sarcosine, and a hydrophobic block comprising a polylactic acid chain. The hydrophilic block and the hydrophobic block are linked together by a linker part.

[1-1. Hydrophilic Block]

In the present invention, the specific degree of the physical property, "hydrophilicity" of the hydrophilic block of the branched-type amphiphilic block polymer A is not particularly limited, but, at least, the whole hydrophilic block shall be relatively more hydrophilic than a polylactic acid chain as the hydrophobic block that will be described later. Alternatively, the hydrophilic block shall be hydrophilic to such an extent that a copolymer composed of the hydrophilic block and the hydrophobic block can have amphiphilicity as a whole molecule of the copolymer. Alternatively, the hydrophilic block shall be hydrophilic to such an extent that the amphiphilic block polymer A can self-assemble in a solvent to form a self-assembly, particularly, a particulate self-assembly.

The amphiphilic block polymer A according to the present invention has a branched structure in the hydrophilic block. Each of the branches of the hydrophilic block contains sarcosine.

The kinds and ratio of structural units constituting the hydrophilic block are appropriately determined by those skilled in the art so that a resultant block can have such hydrophilicity as described above as a whole. Specifically, the total number of sarcosine units contained in all the branches may be, for example, 2 to 200, 2 to 100, or 2 to 10. Alternatively, the total number of sarcosine units contained in the plurality of hydrophilic blocks may be, for example, 30 to 200 or 50 to 100. The average number of sarcosine units per one branch may be, for example, 1 to 60, 1 to 30, 1 to 10, or 1 to 6. That is, each of the hydrophilic blocks can be formed to contain sarcosine or a polysarcosine chain.

If the number of structural units exceeds the above range, when a molecular assembly is formed, the resultant molecular assembly tends to lack stability. If the number of structural units is less than the above range, a resultant block polymer cannot serve as an amphiphilic block polymer or formation of a molecular assembly tends to be difficult per se.

The number of branches of the hydrophilic block shall be 2 or more, but is preferably 3 or more from the viewpoint of efficiently obtaining a particulate micelle when a molecular assembly is formed. The upper limit of the number of branches of the hydrophilic block is not particularly limited, but is, for example, 27. Particularly, in the present invention, the number of branches of the hydrophilic block is preferably 3.

Sarcosine (i.e., N-methylglycine) is highly water-soluble, and polymer of sarcosine is highly flexible, because said polymer has an N-substituted amide and therefore can be more easily cis-trans isomerized as compared to a normal amide group, and steric hindrance around the $C^\alpha$ carbon atom is low. The use of such a structure as a constituent block is very useful in that the block can have high hydrophilicity as its basic characteristic, or both high hydrophilicity and high flexibility as its basic characteristics.

Further, the hydrophilic block preferably has hydrophilic groups (typified by, for example, hydroxyl groups) at its end (i.e., at the end opposite to the linker part).

In the polysarcosine chain, all the sarcosine units may be either continuous or discontinuous. However, it is preferred that the polypeptide chain is molecularly-designed so that the basic characteristics thereof described above are not impaired as a whole.

[1-2. Hydrophobic Block]

In the present invention, the specific degree of the physical property, "hydrophobicity" of the hydrophobic block is not particularly limited, but, at least, the hydrophobic block shall be hydrophobic enough to be a region relatively more hydrophobic than the whole hydrophilic block so that a copolymer composed of the hydrophilic block and the hydrophobic block can have amphiphilicity as a whole molecule of the copolymer, or so that the amphiphilic block polymer A can self-assemble in a solvent to form a self-assembly, preferably a particulate self-assembly.

The hydrophobic block present in one amphiphilic block polymer A may or may not be branched. However, it is considered that a stable core/shell-type molecular assembly having a smaller particle diameter is easily formed when the hydrophobic block is not branched because the density of the hydrophilic branched shell part becomes higher than that of the hydrophobic core part of the molecular assembly.

In the present invention, the hydrophobic block contains a polylactic acid chain (A-PLA). The kinds and ratio of structural units constituting the hydrophobic block are appropriately determined by those skilled in the art so that a resultant block can have such hydrophobicity as described above as a whole. Specifically, for example, when the hydrophobic block is not branched, the number of lactic acid units may be, for example, 5 to 100, 15 to 60, or 25 to 45. When the hydrophobic block is branched, the total number of lactic acid units contained in all the branches may be, for example, 10 to 400, and preferably 20 to 200. In this case, the average number of lactic acid units per one branch is, for example, 5 to 100, and preferably 10 to 100.

If the number of structural units exceeds the above range, when a molecular assembly is formed, the resultant molecular assembly tends to lack stability. If the number of structural units is less than the above range, formation of a molecular assembly tends to be difficult per se.

When the hydrophobic block is branched, the number of branches is not particularly limited, but may be, for example, equal to or less than the number of branches of the hydrophilic block from the viewpoint of efficiently obtaining a particulate micelle when a molecular assembly is formed.

Polylactic acid has the following basic characteristics.

Polylactic acid has excellent biocompatibility and stability. Therefore, a molecular assembly obtained from the amphiphilic material containing polylactic acid as a constituent block is very useful from the viewpoint of applicability to a living body, especially a human body.

Further, polylactic acid is rapidly metabolized due to its excellent biodegradability, and is therefore less likely to accumulate in tissue other than cancer tissue in a living body. Therefore, a molecular assembly obtained from the amphiphilic material containing polylactic acid as a constituent block is very useful from the viewpoint of specific accumulation in cancer tissue.

Further, polylactic acid is excellent in solubility in low-boiling point solvents. This makes it possible to avoid the use of a hazardous high-boiling point solvent when a molecular assembly is produced from the amphiphilic material containing polylactic acid as a constituent block. Therefore, such a molecular assembly is very useful from the viewpoint of safety for a living body.

In the polylactic acid chain (A-PLA) constituting the hydrophobic block, all the lactic acid units may be either continuous or discontinuous. However, it is preferred that the polypeptide chain is molecularly-designed so that the basic characteristics thereof described above are not impaired as a whole.

The polylactic acid chain (A-PLA) constituting the hydrophobic block is a poly-L-lactic acid chain (A-PLLA) comprising L-lactic acid units or a poly-D-lactic acid chain (A-PDLA) comprising D-lactic acid units in order to sterically interact with a polylactic acid chain (F-PLA) contained in a functional substance F that will be described later.

Here, the poly-L-lactic acid chain (A-PLLA) comprising L-lactic acid units means that the ratio of L-lactic acid units to total lactic acid units constituting the polylactic acid chain (A-PLA) is 90% or more, preferably 95% or more, more preferably 98% or more, and particularly preferably 100%. When having such a structure, the poly-L-lactic acid chain (A-PLLA) is expected to form a stereocomplex with a poly-D-lactic acid chain (F-PDLA) contained in the functional substance F.

The poly-D-lactic acid chain (A-PDLA) comprising D-lactic acid units means that the ratio of D-lactic acid units to total lactic acid units constituting the polylactic acid chain (A-PLA) is 90% or more, preferably 95% or more, more preferably 98% or more, and particularly preferably 100%. When having such a structure, the poly-D-lactic acid chain (A-PDLA) is expected to form a stereocomplex with a poly-L-lactic acid chain (F-PLLA) contained in the functional substance F.

[1-3. Ratio of Number of Sarcosine Units to Number of Lactic Acid Units]

In the amphiphilic block polymer A, when the number of sarcosine units (i.e., the total number of sarcosine units contained in all the branches of the hydrophilic block) is defined as $N^S$ and the number of lactic acid units (i.e., the number of lactic acid units contained in the hydrophobic block, or the total number of lactic acid units contained in all the branches when the hydrophobic block is branched) is defined as $N^L$, the ratio of $N^S/N^L$ may be, for example, 0.05 to 5 or 0.05 to 4.

More preferably, the ratio of $N^S/N^L$ may be 0.05 or more and less than 1.8, for example, 0.05 or more and 1.7 or less, 0.05 or more and 1.67 or less, 0.1 or more and 1.7 or less, or 0.1 or more and 1.67 or less.

[1-4. Branched Structure]

The structure of the linker site that links the hydrophilic block and the hydrophobic block together is not particularly limited as long as it is a chemically acceptable structure.

For example, when the number of branches of the hydrophilic block side is 2, two molecular chains containing a polysarcosine chain may extend as branches from one N atom present in the linker site of a molecular chain containing a polylactic acid chain. In other words, an N atom directly or indirectly bound to a polylactic acid chain may be directly or indirectly bound to two polysarcosine chains.

Further, for example, when the number of branches of the hydrophilic block side is 3, three molecular chains containing a polysarcosine chain may extend as branches from one C atom present in the linker site of a molecular chain containing a polylactic acid chain. In other words, a C atom directly or indirectly bound to a polylactic acid chain may be directly or indirectly bound to three polysarcosine chains. The same applies when branching occurs at one P or Si atom present in the linker site, or when the whole molecule of the amphiphilic block polymer forms a quaternary ammonium molecule.

When the number of branches of the hydrophilic block side exceeds 3, the hydrophilic block side can be molecularly-designed so that the branches further have a branched structure.

When the hydrophobic block side is also branched, the hydrophobic block side can be molecularly-designed from the same viewpoint as described above.

A preferred structure of the branched-type amphiphilic block polymer in which the number of branches of the hydrophilic block side is 3 and the hydrophobic block side is not branched is represented by the following formula (I).

[Chemical formula 2]

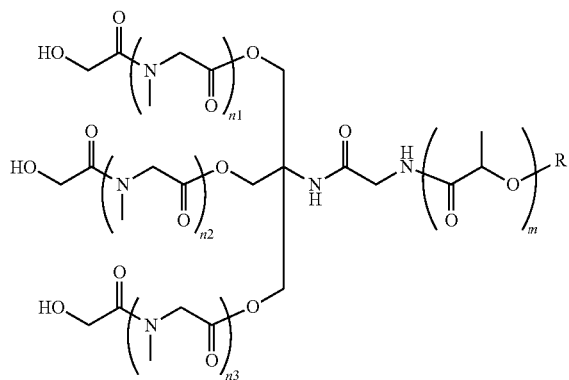

(I)

In the formula (I), n1, n2 and n3 represent numbers whose sum is 3 to 200, m represents a number of 5 to 100, and R represents a hydrogen atom or an organic group. The number of carbon atoms in the organic group may be 1 to 20. Specific examples of the organic group include alkyl groups, alkylcarbonyl groups, and the like.

A preferred structure of the branched-type amphiphilic block polymer in which the number of branches of the hydrophilic block side is 3 and the number of branches of the hydrophobic block side is 2 is represented by the following formula (II).

[Chemical formula 3]

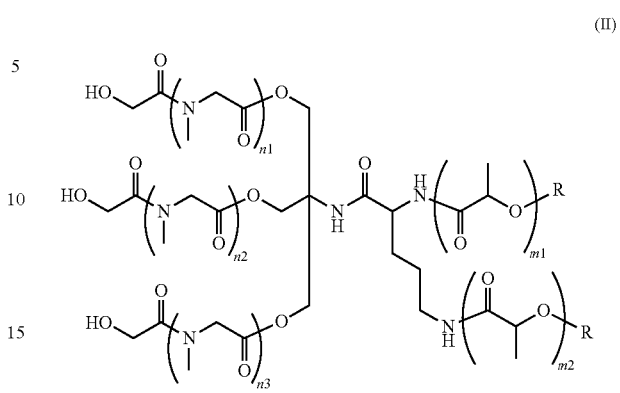

(II)

In the formula (II), n1, n2 and n3 and R are the same as those in the formula (I) and m1 and m2 represent numbers whose sum is 10 to 400.

[1-5. Synthesis Method of Branched-Type Amphiphilic Block Polymer A]

In the synthesis of the branched-type amphiphilic block polymer, the synthesis of a hydrophobic block part (polylactic acid part), the synthesis of a hydrophilic block part (sarcosine part or polysarcosine part), and the synthesis of a linker part that links these blocks together are performed.

The branched-type amphiphilic block polymer can be synthesized by, for example, synthesizing a linker reagent that links sarcosine or polysarcosine chains and a polylactic acid chain(s) together, and then using the linker reagent as an initiator to perform attachment of a sarcosine site or extension of a polysarcosine site by polymerization reaction and extension of a polylactic acid site by polymerization reaction.

Further, the branched-type amphiphilic block polymer can be synthesized by, for example, extending a polylactic acid chain(s) after attachment of sarcosine to a linker reagent, or after attachment of polysarcosine chains, previously prepared as a hydrophilic block by polymerization reaction, to a linker reagent.

Furthermore, the branched-type amphiphilic block polymer can be synthesized by, for example, previously preparing both sarcosine or polysarcosine chains and polylactic acid chains as a hydrophilic block and a hydrophobic block, respectively, and linking these blocks together using a linker reagent separately synthesized.

The linker reagent can have a structure in which the number of functional groups (e.g., hydroxyl groups, amino groups or the like) that can be bound to a lactic acid monomer (lactic acid or lactide) or a polylactic acid chain is one or equal to the desired number of branches of the hydrophobic block side and the number of functional groups (e.g., amino groups) that can be bound to a sarcosine monomer (e.g., sarcosine or N-carboxysarcosine anhydride) or polysarcosine is equal to the desired number of branches of the hydrophilic block side. In this case, the linker reagent is appropriately molecularly-designed by those skilled in the art so that each of the functional groups that can be bound to a sarcosine monomer or polysarcosine has the same reactivity as much as possible.

The functional group that can be bound to a lactic acid monomer or a polylactic acid chain and the functional group that can be bound to a sarcosine monomer or polysarcosine may each be protected with a protective group. In this case, as their respective protective groups, those that can be selectively removed if necessary are appropriately selected by those skilled in the art.

For example, a linker reagent used to synthesize the branched-type amphiphilic block polymer whose number of branches of the hydrophilic block side is 3 can be prepared based on, for example, a tris(hydroxymethyl)aminomethane (Tris) structure.

Further, in the case of allowing the hydrophobic block side to be branched, a linker reagent can be prepared based on, for example, a structure having a larger number of branching points than the tris(hydroxymethyl)aminomethane structure. The structure having a larger number of branching points can be obtained in the following manner: a derivative of amino acid (specific examples thereof include lysine and ornithine) having, in its side chain, an amino group as an example of a functional group that can be bound to a polylactic acid chain, in which all the amino groups are protected, is attached to tris(hydroxymethyl)aminomethane, and then deprotection is performed. The number of branching points can be increased by further attaching such an amino acid derivative to free amino groups obtained by deprotection.

A method for synthesizing the polysarcosine chain or the polylactic acid chain can be appropriately determined by those skilled in the art depending on the kind of functional group in a linker reagent, and may be selected from known peptide synthesis methods or polyester synthesis methods.

Peptide synthesis is preferably performed by, for example, ring-opening polymerization of N-carboxysarcosine anhydride (sarcosine NCA) using, as an initiator, a basic group, such as an amino group, in a linker reagent.

Polyester synthesis is preferably performed by, for example, ring-opening polymerization of lactide using, as an initiator, a basic group, such as an amino group, in a linker reagent.

When a branched-type amphiphilic block polymer different in the number of branches from the above specific example is synthesized, the branched-type amphiphilic block polymer can be prepared by those skilled in the art with appropriately making various changes in terms of organic chemistry.

The chain length of the polysarcosine chain or the polylactic acid chain can be adjusted by adjusting a loading ratio between the initiator and the monomer in the polymerization reaction. The chain length can be also determined by, for example, $^1$HNMR.

[2. Functional Substance F Comprising Functional Site and Polylactic Acid Chain]

A molecular assembly according to the present invention contains a functional substance F comprising a functional site and a polylactic acid chain. The functional substance F is a hydrophobic compound, and is located in the hydrophobic core part of the molecular assembly so as to be encapsulated in the molecular assembly. Therefore, the molecular assembly according to the present invention is a useful structure as a probe for molecular imaging or a pharmaceutical preparation for drug delivery system.

[2-1. Functional Site]

The functional site of the functional substance F is a site (group) selected from the group consisting of a labeling agent (signal agent) and a drug.

As the signal agent, a molecule having the following signal group can be used. A signal group is a group having a property detectable for imaging. Examples of such a signal group include fluorescent groups, radioactive element-containing groups, and magnetic groups. Means for detecting these groups may be appropriately selected by those skilled in the art.

Examples of the fluorescent groups include, but are not limited to, groups derived from fluorescein-based dyes, cyanine-based dyes such as indocyanine dyes, rhodamine-based dyes, and quantum dots. In the present invention, near-infrared fluorescent groups (e.g., groups derived from cyanine-based dyes or quantum dots) are preferably used.

Each substituent group having a hydrogen bond exhibits absorption in the near-infrared region (700 to 1300 nm), but the degree of absorption is relatively small. Therefore, near-infrared light easily penetrates through living tissue. It can be said that by utilizing such characteristics of near-infrared light, in-vivo information can be obtained without putting an unnecessary load on the body. Particularly, when a target to be measured is decided to a site close to the body surface of a small animal, near-infrared fluorescence can give useful information.

More specific examples of the near-infrared fluorescent groups include groups derived from indocyanine dyes such as ICG (indocyanine green), Cy7, DY776, DY750, Alexa790, Alexa750, and the like. In a case where the molecular assembly according to the present invention is intended for use targeting, for example, cancer, groups derived from an indocyanine dye such as ICG may be particularly preferably used from the viewpoint of accumulation in a cancer.

Examples of the radioactive element-containing groups include, but are not limited to, groups derived from saccharides, amino acids, or nucleic acids labeled with a radioisotope such as $^{18}$F. One specific example of a method for introducing a radioactive element-containing group includes a method comprising the step of polymerizing lactide using mono-Fmoc (9-fluorenylmethyloxycarbonyl)ethylenediamine, the step of protecting a terminal OH group by a silyl protecting group, the step of eliminating Fmoc by piperidine treatment, the step of polymerizing sarcosine-N-carboxyanhydride (SarNCA) and terminating the end of the polymer, the step of eliminating the silyl protecting group to perform conversion to a sulfonate ester (e.g., trifluoromethanesulfonate ester, p-toluenesulfonate ester), and the step of introducing a radioactive element-containing group. If necessary, this specific example may be modified by those skilled in the art.

Examples of the magnetic groups include, but are not limited to, groups having a magnetic substance such as ferrichrome and groups contained in ferrite nanoparticles and magnetic nanoparticles.

Among them, near-infrared fluorescent substances such as indocyanine green-based dyes, or radioactive element-containing substances such as saccharides, amino acids, or nucleic acids labeled with a radioisotope such as $^{18}$F may be preferably used in the present invention. These labeling agents may be used singly or in combination of two or more thereof.

As the drug, one suitable for a target disease is appropriately selected by those skilled in the art. Specific examples of the drug include anticancer drugs, antimicrobial agents, antiviral agents, anti-inflammatory agents, immunosuppressive drugs, steroid drugs, hormone drugs, anti-angiogenic agents, and the like. These drug molecules may be used singly or in combination of two or more thereof.

[2-2. Polylactic Acid Chain]

The functional substance F to be encapsulated in the molecular assembly comprises the above-described site (group) selected from the group consisting of a labeling agent (signal agent) and a drug, and a polylactic acid chain (F-PLA) (group) bound to the site (group).

The polylactic acid chain (F-PLA) constituting the functional substance F is a poly-D-lactic acid chain (F-PDLA) comprising D-lactic acid units or a poly-L-lactic acid chain (F-PLLA) comprising L-lactic acid units to sterically interact with the above-described polylactic acid chain (A-PLA) constituting the hydrophobic block.

Here, the poly-D-lactic acid chain (F-PDLA) comprising D-lactic acid units means that the ratio of D-lactic acid units to total lactic acid units constituting the polylactic acid chain (F-PLA) is 90% or more, preferably 95% or more, more preferably 98% or more, and particularly preferably 100%. When having such a structure, the poly-D-lactic acid chain (F-PDLA) is expected to forma stereocomplex with the poly-L-lactic acid chain (A-PLLA) constituting the hydrophobic block.

Here, the poly-L-lactic acid chain (F-PLLA) comprising L-lactic acid units means that the ratio of L-lactic acid units to total lactic acid units constituting the polylactic acid chain (F-PLA) is 90% or more, preferably 95% or more, more preferably 98% or more, and particularly preferably 100%. When having such a structure, the poly-L-lactic acid chain (F-PLLA) is expected to forma stereocomplex with the poly-D-lactic acid chain (A-PDLA) constituting the hydrophobic block.

The number of lactic acid units of the polylactic acid chain constituting the functional substance F is 15 to 60, and preferably 25 to 45. Within the above range, the polylactic acid-bound functional substance F is molecularly-designed so that its entire length does not exceed the length of the above-described amphiphilic block polymer A. Preferably, the polylactic acid-bound functional substance F is molecularly-designed so that its entire length does not exceed twice the length of the hydrophobic block of the amphiphilic block polymer A. If the number of structural units exceeds the above range, when a molecular assembly is formed, the resultant molecular assembly tends to lack stability. If the number of structural units is less than the above range, the affinity of the functional substance F for the hydrophobic block of the amphiphilic block polymer A, especially stereocomplex formation, tends to be lowered.

The amount of the functional substance F encapsulated is not particularly limited, but for example, the functional substance F is encapsulated in an amount of 20 mol % or less, preferably 0.5 to 20 mol %, and more preferably 1.0 to 20 mol % with respect to the amount of the amphiphilic block polymer A. If the amount of the functional substance F encapsulated exceeds 20 mol %, the particle diameter of the molecular assembly tends to exceed 30 nm or primary particles of the molecular assembly tend to aggregate.

[3. Molecular Assembly]

[3-1. Molecular Assembly]

A molecular assembly (lactosome) according to the present invention is a structure formed by aggregation or self-assembling orientation of the above described branched-type amphiphilic block polymer A. The molecular assembly according to the present invention is preferably a micelle constituted to have a hydrophobic block on the inside (core) and a hydrophilic block on the outside (shell) in terms of practical use. The molecular assembly according to the present invention is allowed to have an appropriate functional structure (the functional substance F comprising a functional site and a polylactic acid chain) so as to be a useful structure as a probe for molecular imaging or a preparation for a drug delivery system.

The branched-type amphiphilic block polymer A is larger in the molecular cross-sectional area of a hydrophilic site than a linear amphiphilic block polymer due to the presence of a plurality of polysarcosine chains as branched chains. Therefore, the molecular assembly composed of the branched-type amphiphilic block polymer is excellent in stability as a particle. Further, such a particle can have a large curvature. Therefore, as will be described later, the molecular assembly according to the present invention has a basic characteristic that said molecular assembly can have a reduced particle size.

Further, the molecular assembly composed of the branched-type amphiphilic block polymer A has a basic characteristic that said molecular assembly has a higher hydrophilic group density on the surface than conventional lactosomes due to the presence of a plurality of polysarcosine chains as branched chains, and therefore hydrophobic site in said molecular assembly is less exposed.

It is to be noted that in the molecular assembly according to the present invention, a small amount of a linear type amphiphilic block polymer whose hydrophilic block is not branched may be used in combination with the branched-type amphiphilic block polymer A in a range where the effects of the present invention are not impaired. However, when the linear type amphiphilic block polymer is used, attention should be paid because the particle diameter of the molecular assembly tends to increase. The mixing ratio between the branched-type amphiphilic block polymer and the linear type amphiphilic block polymer may be 50:50 to 100:0, preferably 67:33 to 100:0, and more preferably 95:5 to 100:0 on molar basis. Also in this case, the stereochemistry of the polylactic acid chain (A-PLA) constituting the hydrophobic block is the same as described above.

[3-2. Particle Diameter]

The particle diameter of the molecular assembly according to the present invention may be, for example, 10 to 30 nm. The upper limit within this range may be 28 nm, 25 nm, or 23 nm. The lower limit may be 15 nm. In the present invention, a molecular assembly having a particle diameter smaller than the lower limit of the above range may also be obtained by shortening the chain length of the branched-type amphiphilic block polymer A. The term "particle size" used herein refers to a particle size occurring most frequently in particle size distribution, that is, a mode particle size. As has been described above, the molecular assembly according to the present invention basically tends to have a smaller particle size than conventional ones due to the branched structure of the hydrophilic block of the amphiphilic block polymer.

When exceeding the upper limit of the above range, the particle diameter of the molecular assembly is not so much different from that of a molecular assembly composed of a linear type amphiphilic block polymer (WO 2009/148121: 30 nm or more). In this case, it is difficult to obtain a preferred EPR effect when the molecular assembly is administered as a molecular probe into a living body.

Examples of a method for controlling the particle diameter include a method in which the chain length of the branched-type amphiphilic block polymer A of the molecular assembly is shortened to adjust the particle diameter to be smaller; a method in which the liner-type amphiphilic block polymer is not used, or the amount of the linear type amphiphilic block polymer to be blended is reduced as much as possible to adjust the particle diameter to be smaller; a method in which the amount of the functional substance F is reduced to adjust the particle diameter to be smaller, and the like.

A method for measuring the size of the molecular assembly according to the present invention is not particularly limited, and is appropriately selected by those skilled in the art. Examples of such a method include an observational method with a TEM (Transmission Electron Microscope) or an AFM (Atomic Force Microscope), and a DLS (Dynamic Light Scattering) method. In the case of a DLS method, the translational diffusion coefficient of particles undergoing Brownian movement in a solution is measured.

[3-3. Formation of Molecular Assembly]

A method for forming the molecular assembly is not particularly limited, and can be appropriately selected by those skilled in the art depending on, for example, the desired size and characteristics of the molecular assembly and the kind, properties, and amount of a functional structure to be carried by the molecular assembly. If necessary, after being formed by a method that will be described later, the resultant molecular assemblies may be surface-modified by a known method. It is to be noted that whether particles have been formed or not may be confirmed by observation with an electron microscope.

[3-3-1. Film Method]

The branched-amphiphilic block polymer A according to the present invention is soluble in low-boiling point solvents, and therefore the molecular assembly can be prepared by a film method.

The film method includes the following steps:

preparing a solution, in a container (e.g., a glass container), containing the branched-type amphiphilic block polymer A and the functional substance F in an organic solvent;

removing the organic solvent from the solution to obtain a film comprising the branched-type amphiphilic block polymer A and the functional substance F on an inner wall of the container; and adding water or an aqueous solution into the container and performing ultrasonic treatment or warming treatment to convert the film-like substance into a molecular assembly (a molecular assembly encapsulating the functional substance F), thereby obtaining a dispersion liquid of the molecular assembly. The film method may further include the step of subjecting the dispersion liquid of the molecular assembly to freeze-drying treatment.

The solution containing the branched-type amphiphilic block polymer A and the functional substance F in an organic solvent may be prepared by previously preparing a film comprising only the branched-type amphiphilic block polymer A, and then adding a solution containing the functional substance F to the film for dissolution at the time of nanoparticle preparation.

Preferred examples of the organic solvent used in the film method include low-boiling point solvents. In the present invention, the term "low-boiling point solvent" refers to one whose boiling point is 100° C. or less, and preferably 90° C. or less at 1 atmospheric pressure. Specific examples of such a low-boiling point solvent include chloroform, diethyl ether, acetonitrile, methanol, ethanol, acetone, dichloromethane, tetrahydrofuran, hexane, and the like.

The use of such a low-boiling point solvent makes it very easy to perform solvent removal. A method for solvent removal is not particularly limited, and may be appropriately determined by those skilled in the art depending on the boiling point of an organic solvent to be used, or the like. For example, solvent removal may be performed under reduced pressure or by natural drying.

After the organic solvent is removed, a film containing the branched-type amphiphilic block polymer A and the functional substance F is formed on the inner wall of the container. Water or an aqueous solution is added to the container to which the film is attached. The water or aqueous solution is not particularly limited, and biochemically or pharmaceutically acceptable ones may be appropriately selected by those skilled in the art. Examples thereof include distilled water for injection, normal saline, a buffered solution, and the like.

After water or an aqueous solution is added, warming treatment is performed. The film is peeled off from the inner wall of the container by warming, and in this process, the molecular assembly is formed. The warming treatment can be performed under conditions of, for example, 70 to 100° C. and 5 to 60 minutes. After the completion of the warming treatment, a dispersion liquid in which the molecular assembly (the molecular assembly encapsulating the functional substance F) is dispersed in the water or aqueous solution is prepared in the container. Further, if necessary, ultrasonic treatment may be performed in combination when the film is peeled off.

The obtained dispersion liquid can be directly administered to a living body. That is, the molecular assembly does not need to be stored by itself under solvent-free conditions.

On the other hand, the obtained dispersion liquid may be subjected to freeze-drying treatment. A method for freeze-drying treatment is not particularly limited, and any known method can be used. For example, the dispersion liquid of the molecular assembly obtained in such a manner as described above may be frozen by liquid nitrogen and sublimated under reduced pressure. In this way, a freeze-dried product of the molecular assembly is obtained. That is, the molecular assembly can be stored as a freeze-dried product. If necessary, water or an aqueous solution may be added to the freeze-dried product to obtain a dispersion liquid of the molecular assembly, and the molecular assembly can be used. The water or aqueous solution is not particularly limited, and biochemically or pharmaceutically acceptable ones may be appropriately selected by those skilled in the art. Examples thereof include distilled water for injection, normal saline, a buffer solution, and the like.

[3-3-2. Injection Method]

An injection method includes the following steps:

preparing a solution, in a container (e.g., a test tube), containing the branched-type amphiphilic block polymer A and the functional substance F in an organic solvent;

dispersing the solution in water or an aqueous solution; and removing the organic solvent. In the injection method, the step of purification treatment may be appropriately performed before the step of removing the organic solvent.

Examples of the organic solvent used in the injection method include trifluoroethanol, ethanol, hexafluoroisopropanol, dimethylsulfoxide, dimethylformamide, and the like. Examples of the water or aqueous solution used include distilled water for injection, normal saline, a buffer solution and the like.

Examples of the purification treatment performed include gel filtration chromatography, filtering, ultracentrifugation, and the like.

[4. Drug Delivery System and Molecular Imaging]

[4-1. Object to which Molecular Assembly is to be Administered]

A drug delivery system and molecular imaging according to the present invention include administration of the above-described molecular assembly to a living body. The living body to which the molecular assembly is administered is not particularly limited, but may be a human or a non-human animal. The non-human animal is not particularly limited, and may be a mammal other than a human. Specific examples thereof include primates, gnawing mammals (e.g., mice, rats), rabbits, dogs, cats, pigs, bovines, sheep, horses, and the like.

The molecular assembly used in the method according to the present invention is excellent in specific accumulation in a vascular lesion site (e.g., a malignant tumor site, an inflammatory site, an arterial sclerosis site, an angiogenic site). The molecular assembly according to the present invention accumulates in the tissue of such a site due to EPR (enhanced permeability and retention) effect, and therefore its accumulation does not depend on the kind of tissue of a vascular lesion site. The administration target of the fluorescent probe according to the present invention is preferably a cancer. Examples of the cancer as the administration target include a wide variety of cancers such as liver cancers, pancreas cancers, lung cancers, uterine cervical cancers, breast cancers, and colon cancers.

[4-2. Administration]

A method for administration to a living body is not particularly limited, and can be appropriately determined by those skilled in the art. Therefore, the administration method may be either systemic or local. That is, the molecular probes can be administered by any one of injection (needle injection or needleless injection), oral administration, and external administration.

The molecular assembly according to the present invention has a dense polymer brush structure of sarcosine chains in its particle surface due to the branched structure of the branched-type amphiphilic block polymer A as its essential component. Therefore, it is considered that, as compared to conventional lactosomes, the hydrophobic site of the particle is less exposed to an external environment, and therefore the recognition of the particle as a foreign substance by the external environment is suppressed. The molecular assembly according to the present invention makes it possible to achieve a reduction in ABC phenomenon believed to be due to this matter. Therefore, the molecular assembly according to the present invention can be administered more than once. For example, the molecular assemblies according to the present invention may be administered to the same individual two or more necessary times (e.g., 2 to 10 times). Further, the span between administrations may be, for example, 1 to 60 days.

In the molecular assembly according to the present invention, the stereochemistry of the polylactic acid chain (A-PLA) constituting the hydrophobic block of the amphiphilic block polymer A and the stereochemistry of the polylactic acid chain (F-PLA) contained in the functional substance F are made different from each other. This allows the polylactic acid chain (A-PLA) and the polylactic acid chain (F-PLA) to form a stereocomplex with each other so that the molecular assembly maintains its stability despite its small particle diameter of less than 30 nm. Further, it is considered that the helix structure of the polylactic acid chain (A-PLA) and the helix structure of the polylactic acid chain (F-PLA) are different from each other, and the hydrophobic functional site bound to the polylactic acid chain (F-PLA) is easily retained in the hydrophobic inside of the molecular assembly having a core/shell structure so that the stability of the molecular assembly is further improved. These effects allow the labeling agent (signal agent) or drug encapsulated in the molecular assembly is retained in a target cancer site for a long time after the molecular assembly is delivered to the target site. Therefore, the molecular assembly is expected to be delivered to a small lesion site and to exhibit a drug effect for a longer time.

[4-3. Detection of Molecular Assembly]

The molecular imaging according to the present invention includes the step of detecting signals derived from the administered molecular assembly. By detecting the administered molecular assembly, it is possible to observe the appearances of an administration target (especially, the position and size of cancer tissue, and the like) from outside the body.

As a detection method, any means that can visualize the administered molecular assembly can be used. The detection means can be appropriately determined by those skilled in the art depending on the kind of signal group or signal substance of the molecular assembly.

When the particle size of the molecular assembly is the same as that of a molecular assembly by a conventional method, the time from administration to the start of detection can be appropriately determined by those skilled in the art depending on the kind of the functional substance F of the molecular assembly to be administered and the kind of administration target. For example, detection may be started after a lapse of 1 to 24 hours from administration. If the time is shorter than the above range, a detected signal is too strong, and therefore it tends to be difficult to clearly distinguish an administration target from other sites (background). On the other hand, if the time is longer than the above range, the molecular assembly tends to be excreted from the administration target.

On the other hand, the molecular assembly according to the present invention is excellent in stability as a particle due to the branched structure of the branched-type amphiphilic block polymer A as its essential component; and the specific combination of the stereochemistry of the polylactic acid chain (A-PLA) in the branched-type amphiphilic block polymer A and the stereochemistry of the polylactic acid chain (F-PLA) contained in the functional substance F, and a molecular assembly with a small particle size, which is not previously attainable, can be prepared. When the molecular assembly having a small particle size is administered to a living body, the rate of accumulation of the molecular assembly in target tissue by the EPR effect can be accelerated, and excretion of the molecular assembly to the outside of the body by the kidney can be accelerated. Therefore, when the molecular assembly is smaller in particle size than those by a conventional method, the time from administration to the start of detection can be shortened as compared to a conventional method. For example, the time may be 1 to 24 hours, and preferably 1 to 9 hours. The present invention makes it possible to reduce the particle size of a molecular assembly, and therefore the ratio of contrast at tumor site to background can be increased in a short period of time after intravascular administration so that short-time selective imaging of a cancer site can be achieved.

It is to be noted that from the viewpoint of accuracy, detection of the molecular assembly is preferably performed by measuring a living body not from one direction but from two or more directions. Specifically, a living body may be measured from at least three directions, and more preferably from at least five directions. When measurement is performed from five directions, a living body can be measured from, for example, both right and left abdomen sides, both right and left sides of the body, and a back side.

EXAMPLES

Hereinbelow, the present invention will be described in more detail with reference to examples, but is not limited thereto.

Synthesis Example 1

Synthesis of Branched-Type Amphiphilic Block Polymer

In this example, a branched-type amphiphilic block polymer, in which three polysarcosine (PSar) chains were bound to one polylactic acid (L-polylactic acid: PLLA) chain, was synthesized.

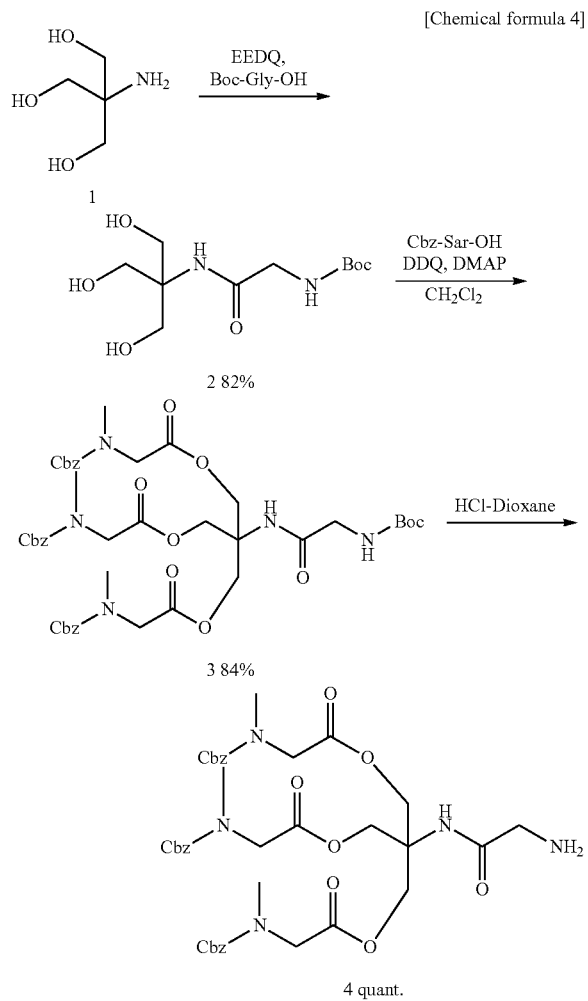

[Chemical formula 4]

As an outline, first, a linker reagent was synthesized. The linker reagent was synthesized from tris hydroxymethyl aminomethane (Tris) 1 having one amino group as an initiator of PLLA polymerization and three hydroxyl groups as an initiator of NCA (N-carboxy anhydride) polymerization in a sarcosine site. Further, appropriate protective groups were attached to the amino group and hydroxyl groups of Tris 1 so that these groups could be deprotected, if necessary. Specifically, the amino group of Tris 1 was protected with a protective group having a Boc group by using N-tert-butoxycarbonylglycine (Boc-Gly-OH) in the presence of 2-ethoxy-1-ethoxycarbonyl-1,2-dihydroquinoline (EEDQ) to obtain a compound 2, and further the hydroxyl groups of the compound 2 were protected with protective groups having a Cbz group by using benzyloxycarbonylsarcosine (Cbz-Sar-OH) in the presence of dichlorodicyanobenzoquinone (DDQ) and dimethylaminopyridine (DMAP) to obtain a compound 3 as a linker reagent. Only the Boc group of the linker reagent 3 was selectively removed for deprotection using HCl-Dioxane to obtain an amino group-containing compound 4.

A specific synthesis procedure is as follows.

[Compound 2]

Boc-glycine (2.5 g, 0.014 mol) and EEDQ (6.0 g, 0.024 mol) were added to an EtOH solution (75 mL) containing tris(hydroxymethyl)aminomethane (1.9 g, 0.016 mol) and stirred under reflux (95° C.) for 4.5 hours. After the completion of reaction, a precipitate was removed with filter paper, EtOH was distilled away under reduced pressure, and then purification was performed by silica gel column chromatography (CHCl$_3$/MeOH mixtures with mixing ratios (v/v) of 1/0, 40/1, and 10/1 were used as eluents in this order). The thus obtained product 2 had a weight of 3.2 g (0.012 mol), and a yield of 82% was achieved.

[Compound 3]

To a mixture of the compound 2 (278 mg, 1.0 mmol), Cbz-Sar-OH (804 mg, 3.6 mmol), DCC (887 mg, 4.3 mmol), and DMAP (26 mg, 0.21 mmol) was added 10 mL of dichloromethane cooled with ice, and then the resultant mixture was stirred at room temperature overnight. After the completion of reaction, washing with ethyl acetate was performed, a white precipitate (urea) was removed, and then purification was performed by silica gel chromatography (n-hexane/ethyl acetate mixtures with mixing ratios (v/v) of 2/1, 1/1, and 1/2 were used as eluents in this order). As a result, a target compound 3 (719 mg) was obtained in a yield of 84%.

[Compound 4]

To the compound 3 (710 mg) cooled with ice was added 4 mol/L HCl/Dioxane (7.0 mL) for dissolution to obtain a reaction solution, and the reaction solution was stirred at room temperature for 5 minutes. Then, the solvent was distilled away from the reaction solution under reduced pressure, and purification was performed by silica gel chromatography (a CHCl$_3$/MeOH mixture with a mixing ratio of 10/0 (v/v) was used as an eluent).

The thus obtained white precipitate was dissolved in chloroform to obtain a solution, and the solution was subjected to phase separation by adding an aqueous 1N NaOH solution to remove an HCl salt from a terminal amino group. Then, the solution was dehydrated with anhydrous magnesium sulfate, and the magnesium sulfate was removed by Celite filtration to obtain a compound 4.

[Chemical formula 5]
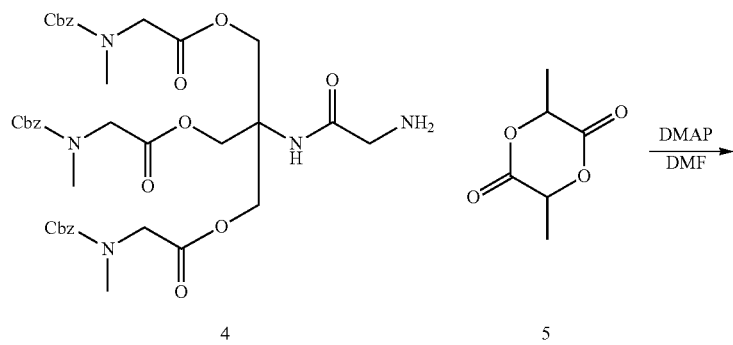
4    5
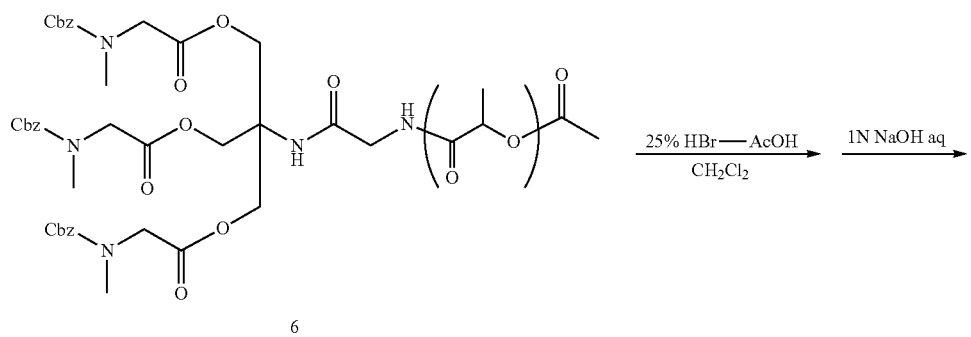
6
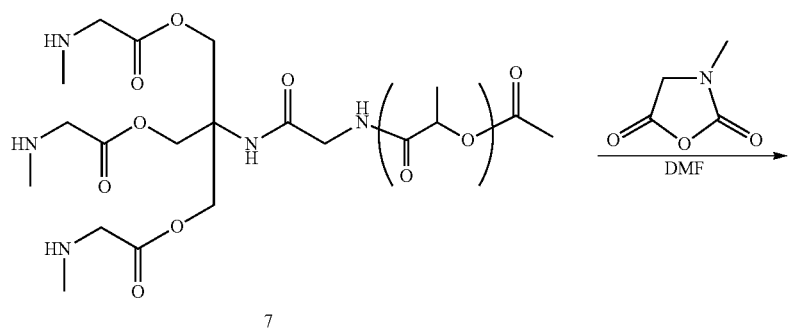
7
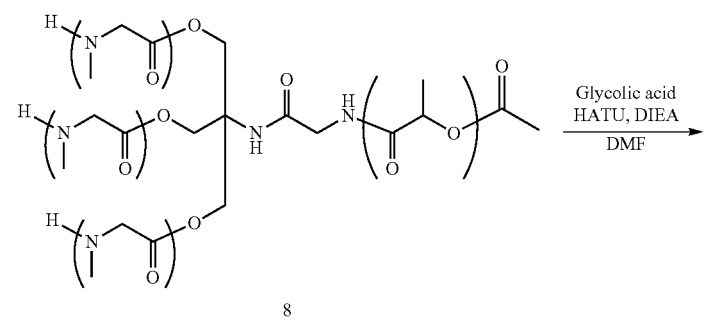
8

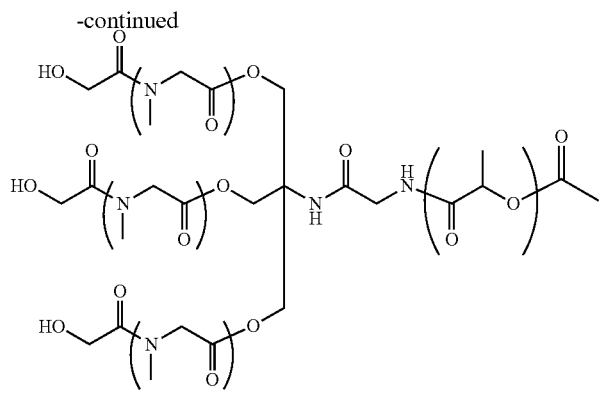

9

Then, lactide 5 was subjected to a polymerization reaction using the amino group-containing compound 4 as an initiator to synthesize a PLLA chain so that a compound 6 was obtained. The Cbz groups remaining as protective groups in the compound 6 were removed with HBr-AcOH for deprotection, and at the same time, the terminal hydroxyl group of PLLA was protected with an acetyl group. Sarcosine-NCA was subjected to N-carboxyanhydride polymerization reaction using three amino groups in a compound 7 as an initiator to synthesize PS chains so that a compound 8 is obtained. Further, glycolic acid, 0-(benzotriazol-1-yl)-N,N,N',N'-tetramethyluroniumhexa-fluorophosphate (HATU), and N,N-diisopropylethylamine (DIEA) were added to the compound 8 to introduce carboxyl groups thereinto so that a branched-type amphiphilic block polymer 9 is obtained. It is to be noted that in the above formula, numbers representing the degree of polymerization are omitted.

A specific synthesis procedure is as follows.

[Compound 6]

To a DMF solution (2 mL) containing the initiator 4 (485 mg, 0.61 mmol) dissolved therein were added 15 equivalents (1.32 g, 9.2 mmol) of L-lactide (5) relative to the initiator 4 and DMAP (75 mg, 0.61 mmol), and then the resultant mixture was stirred at 55° C. in an argon atmosphere overnight (for about 15 hours). The reaction solvent DMF was removed to some extent by distillation under reduced pressure to obtain a concentrate, and the concentrate was then dropped into cold MeOH. The thus obtained white precipitate was collected by centrifugation to obtain a compound 6.

[Compound 7]

The compound 6 was dissolved in 10 mL of dichloromethane to obtain a reaction solution, and the reaction solution was cooled to 0° C., and then 20 mL of 25% HBr-AcOH was added thereto. The reaction solution was stirred at room temperature overnight, and then the solvent was distilled away under reduced pressure so that a white precipitate was obtained. The white precipitate was subjected to NMR measurement, and as a result, it was confirmed that removal of Cbz groups for deprotection had been completed.

The obtained white precipitate was dissolved in chloroform to obtain a solution, and the solution was subjected to phase separation by adding an aqueous 1N NaOH solution to remove an HBr salt from terminal amino groups. Successively, the solution was dehydrated with anhydrous magnesium sulfate, and the magnesium sulfate was removed by Celite filtration to obtain a compound 7.

[Compounds 8 and 9]

A polymerization reaction was performed using the compound 7 as a macroinitiator to form a hydrophilic site. Sar-NCA was added to a DMF solution of the compound 7 in an amount of 40 or 60 equivalents relative to the initiator, and then the concentration of Sar-NCA was adjusted to 0.50 M. The thus obtained reaction solution was stirred at room temperature for 24 hours to obtain a compound 8, and then glycolic acid, HATU, and DIEA were added thereto, and further stirred for 24 hours. After the completion of reaction, the reaction solution was concentrated and then purified by size exclusion chromatography (Sephadex LH20, eluent: DMF) to obtain a target amphiphilic block polymer 9.

The $^1$H NMR measurement result of the obtained amphiphilic block polymer 9 is shown in FIG. 1. From result shown in FIG. 1, the composition of the branched-type amphiphilic block polymer obtained in this synthesis example was identified, and it was found that the number of lactic acid units in the PLLA chain was 30 and the number of sarcosine units per one PSar chain was 34. This amphiphilic block polymer is presented as PLLA30-(Psar34) 3, in terms of average degree of polymerization.

Synthesis Example 2

Synthesis of Z-Poly-L-Lactic Acid (Z-PLLA)

Z-poly-L-lactic acid (Z-PLLA) was synthesized using L-lactide (11) and N-carbobenzoxy-1,2-diaminoethane hydrochloride (12).

[Chemical Formula 6]

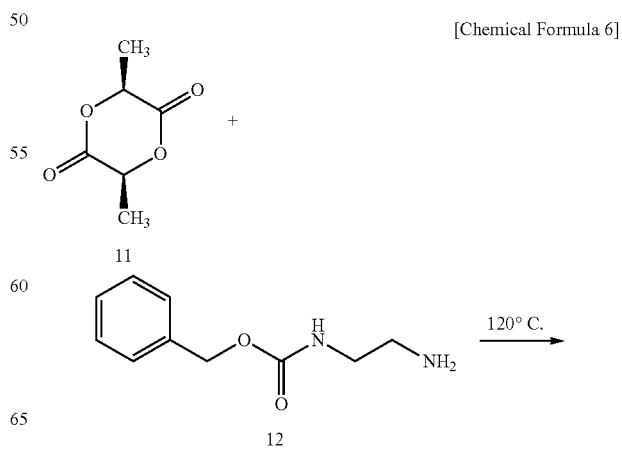

-continued

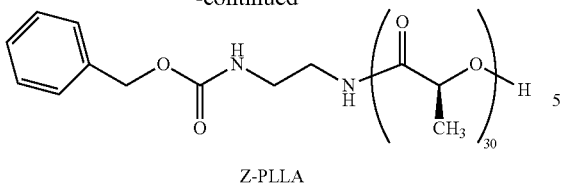

Z-PLLA

To N-carbobenzoxy-1,2-diaminoethane hydrochloride (12) (400 mg, 2.06 mmol) served as a polymerization initiator, a dispersion liquid obtained by dispersing tin octanoate (22.25 mg) in toluene (1.0 mL) was added. The toluene was distilled away under reduced pressure, and then L-lactide (11) (4.45 g, 30.9 mmol) was added to perform polymerization reaction at 120° C. under Ar gas atmosphere. After a lapse of 8 hours, the reaction container was air-cooled to room temperature to obtain a yellowish-white solid. The yellowish-white solid was dissolved in a small amount of dimethylformamide (about 10 mL) and purified using an LH20 column. Then, fractions showing absorption at 270 nm were collected and concentrated to obtain a concentrated liquid, and the concentrated liquid was dissolved in chloroform. The resulting chloroform solution was dropped into cold methanol (100 mL) to obtain a white precipitate. The white precipitate was collected by centrifugation and dried under reduced pressure to obtain a Z-poly-L-Lactic Acid (Z-PLLA30).

Synthesis Example 3

Synthesis of Z-Poly-D-Lactic Acid (Z-PDLA)

Z-poly-D-lactic acid (Z-PDLA30) was obtained in the same manner as in the above-described synthesis of Z-PLLA except that D-lactide (10) was used instead of the L-lactide (11).

[Chemical Formula 7]

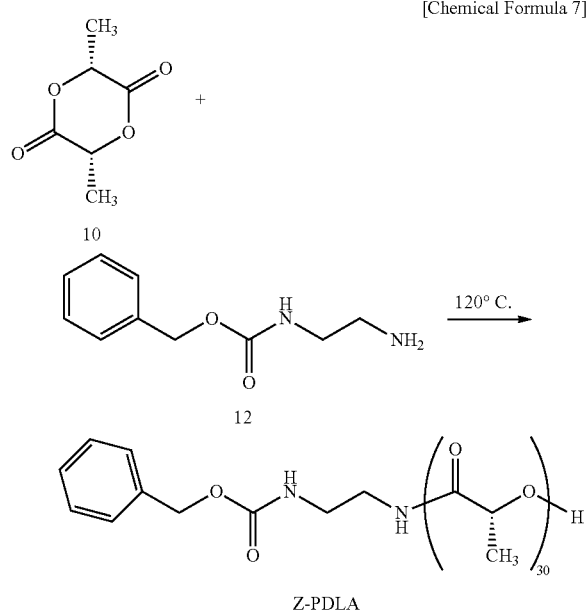

Synthesis Example 4

Synthesis of Aminated Poly-L-Lactic Acid (a-PLLA)

Aminated poly-L-lactic acid (a-PLLA) was synthesized using L-lactide (11) and N-carbobenzoxy-1,2-diaminoethane hydrochloride (12).

[Chemical formula 8]

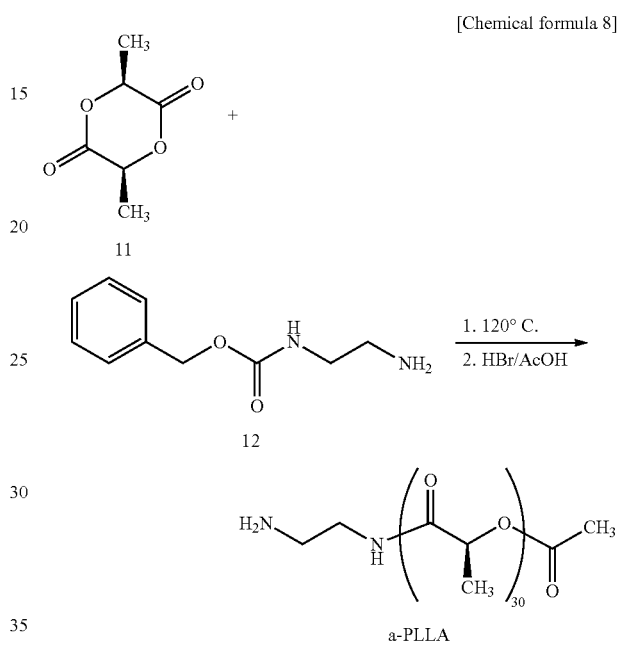

To N-carbobenzoxy-1,2-diaminoethane hydrochloride (12) (310 mg, 1.60 mmol) as a polymerization initiator was added toluene (1.0 mL) in which tin octanoate (6.91 mg) was dispersed. Then, the toluene was distilled away under reduced pressure, and then L-lactide (11) (3.45 g, 24 mmol) was added to perform a polymerization reaction at 120° C. in an Ar atmosphere. After 12 hours, the reaction container was air-cooled to room temperature. The obtained yellowish white solid was dissolved in a small amount of chloroform (about 10 mL). The chloroform was dropped into cold methanol (100 mL) to obtain a white precipitate. The obtained white precipitate was collected by centrifugation and dried under reduced pressure.

To a dichloromethane solution (1 mL) of the obtained white precipitate (500 mg) was added 25 v/v % hydrogen bromide/acetic acid (2.0 mL) to obtain a reaction solution, and the reaction solution was protected from light and stirred for 2 hours in dry air. After the completion of reaction, the reaction solution was dropped into cold methanol (100 mL), and then a deposited precipitate was collected by centrifugation. The obtained white precipitate was dissolved in chloroform, and then washed with a saturated aqueous $NaHCO_3$ solution and dehydrated with anhydrous $MgSO_4$. The $MgSO_4$ was removed by Celite (registered trademark) filtration, and then the resultant product was subjected to vacuum drying to obtain a white amorphous powder of a-PLLA (440 mg). Further, the number of lactic acid units is presented as average degree of polymerization.

Synthesis Example 5

Synthesis of ICG-Labeled Poly-L-Lactic Acid (ICG-PLLA)

The aminated poly-L-lactic acid (a-PLLA) was labeled with ICG to obtain ICG-labeled poly-L-lactic acid (ICG-PLLA). Specifically, a DMF solution containing 1 mg (1.3 eq) of an indocyanine green derivative (ICG-sulfo-OSu) dissolved therein was added to a DMF solution containing 1.9 mg (1.0 eq) of a-PLLA and stirred at room temperature for about 20 hours. Then, the solvent was distilled away under reduced pressure, and purification was performed using an LH20 column to obtain a ICG-labeled poly-L-lactic acid (ICG-PLLA).

Synthesis Example 6

Synthesis of Aminated Poly-D-Lactic Acid (a-PDLA)

Aminated poly-D-lactic acid (a-PDLA) was synthesized in the same manner as in Synthesis Example 4 except that D-lactide was used instead of the L-lactide (11) used in Synthesis Example 4.

Synthesis Example 7

Synthesis of ICG-Labeled Poly-D-Lactic Acid (ICG-PDLA)

ICG-labeled poly-D-lactic acid (ICG-PDLA) was obtained in the same manner as in Synthesis Example 5 except that aminated poly-D-lactic acid (a-PDLA) was used instead of the aminated poly-L-lactic acid (a-PLLA) used in Synthesis Example 5.

[Chemical formula 9]

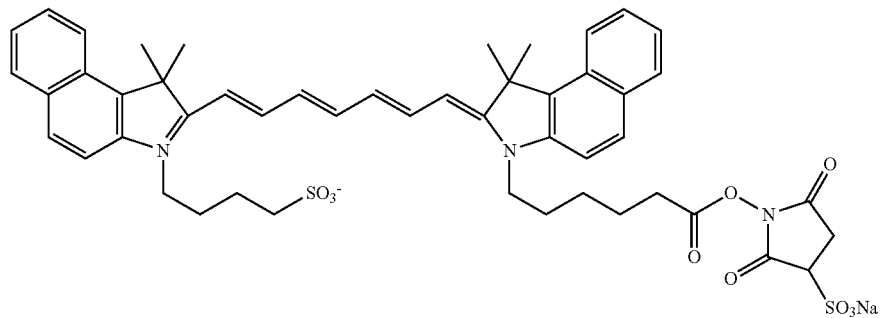

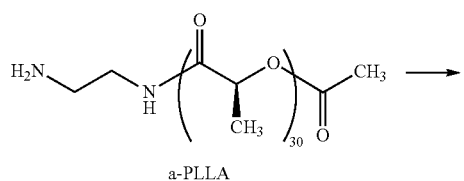

a-PLLA

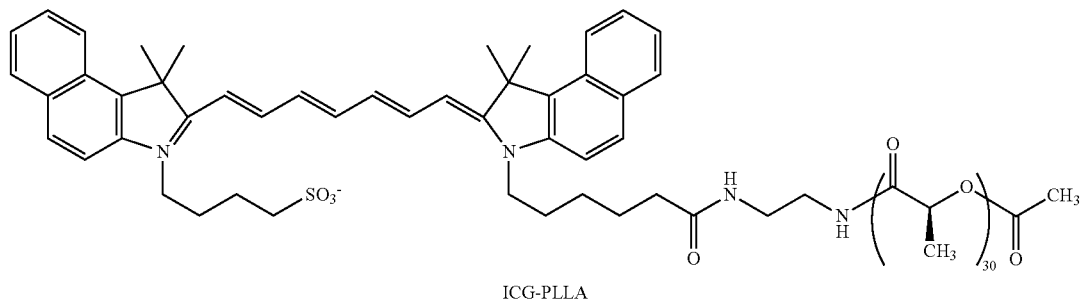

ICG-PLLA

[Chemical formula 10]

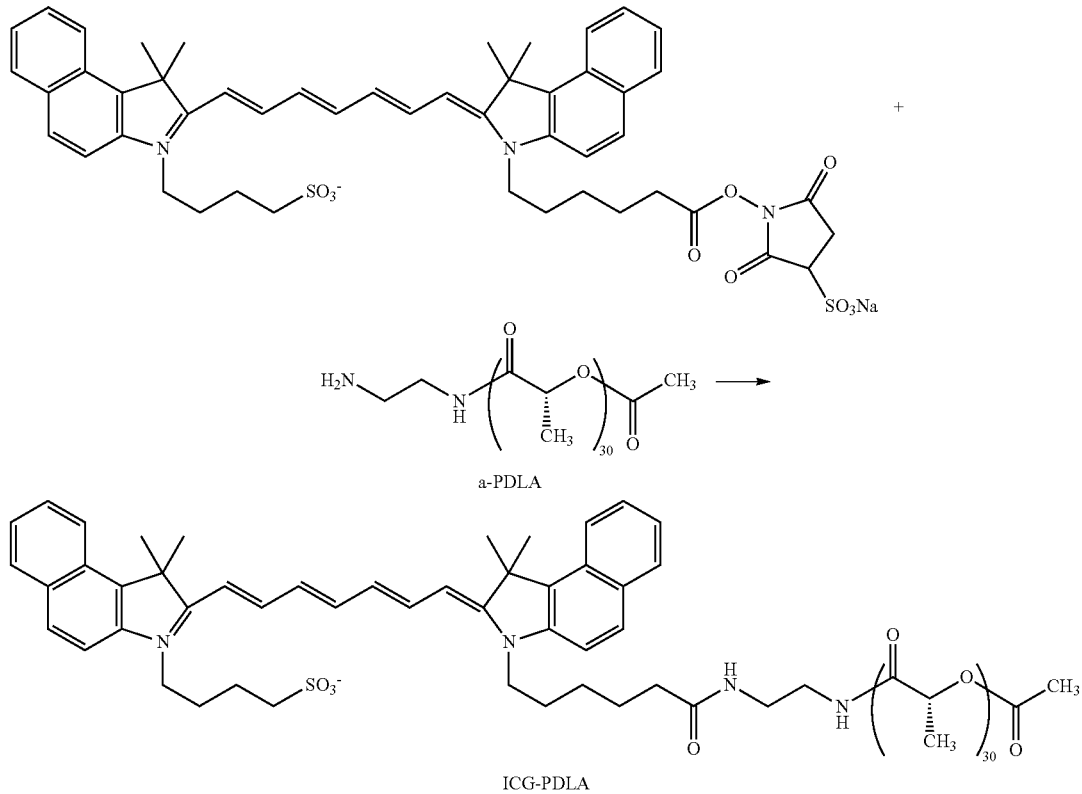

a-PDLA

ICG-PDLA

Synthesis Example 8

Synthesis of Aminated Poly-DL-Lactic Acid (a-PDLLA)

Aminated poly-DL-lactic acid (a-PDLLA) was synthesized in the same manner as in Synthesis Example 4 except that DL-lactide (meso-lactide) was used instead of the L-lactide (11) used in Synthesis Example 4.

Synthesis Example 9

Synthesis of ICG-Labeled Poly-DL-Lactic Acid (ICG-PDLLA)

ICG-labeled poly-DL-lactic acid (ICG-PDLLA) was obtained in the same manner as in Synthesis Example 5 except that aminated poly-DL-lactic acid (a-PDLLA) was used instead of the aminated poly-L-lactic acid (a-PLLA) used in Synthesis Example 5.

Experimental Example 1

Method for Preparing Molecular Assembly Lactosome

As a branched-type amphiphilic block polymer, [PLLA30-(Psar23)3] was used which had a PLLA chain comprising 30 lactic acid units and Psar chains each comprising 23 sarcosine units.

PLLA30-(Psar23)3 (MW=7405) in an amount of 2 to 3 mg was weighed in a glass test tube and dissolved in 0.5 mL of chloroform. Then, the solvent was distilled away under reduced pressure to form a film on the wall surface of the glass test tube. Ultrapure water in an amount of 2 mL was added to the obtained film and was subjected to heat treatment in a hot-water bath at 85° C. for 20 minutes to convert the film into particles. In this way, a dispersion liquid of lactosome particles composed of only the branched-type amphiphilic block polymer, PLLA30-(Psar23)3 was obtained.

Experimental Example 2

Change in Particle Diameter of Lactosome Due to Addition of Polylactic Acid

Lactosome particles were obtained in the same manner as in Experimental Example 1 except that a predetermined amount of the Z-poly-L lactic acid (Z-PLLA30) or the Z-poly-D-lactic acid (Z-PDLA30) was dissolved in chloroform together with the branched-type amphiphilic block polymer, PLLA30-(Psar23)3. In this way, dispersion liquids of lactosome particles were obtained which were different in the stereochemistry of the Z-polylactic acid contained in the lactosome.

Figure 2:
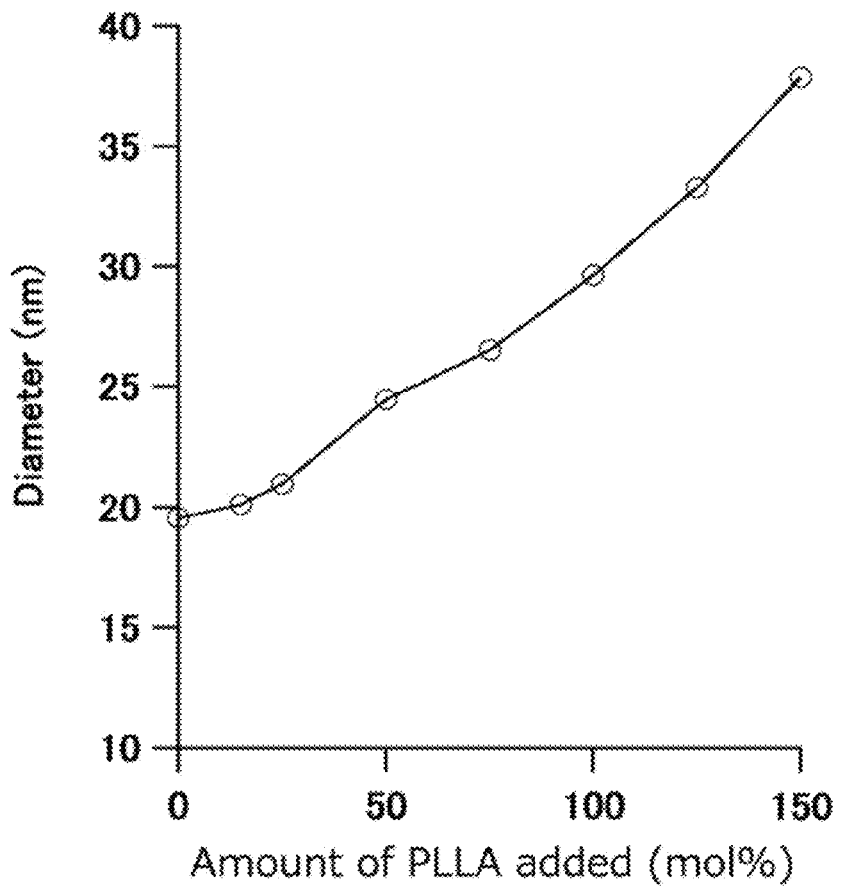
FIG. 2 is a graph showing changes in the particle diameter of a lactosome due to the addition amounts of poly-L-lactic acid (PLLA) in Experimental Example 2.

The amounts of the Z-poly-L-lactic acid (Z-PLLA30) added were 0, 15, 25, 50, 75, 100, 125, and 150 mol % with respect to the amount of the branched-type amphiphilic block polymer, PLLA30-(Psar23)3, respectively. The particle diameter of each of the thus obtained lactosomes was measured by dynamic scattering (DLS) using a dynamic light scattering measuring device (manufactured by Malvern Instruments, Zetasizer Nano). The particle diameters of the obtained lactosomes are shown in FIG. 2. In FIG. 2, the vertical axis represents the particle diameter (Diameter (nm)), and the horizontal axis represents the amount of Z-PLLA30 added (mol %). When Z-PLLA30 having the same stereochemistry as PLLA30-(Psar23)3 was added, the particle diameter was increased as the amount of Z-PLLA30 added was increased. When the amount of Z-PLLA30 added exceeded 100 mol %, the particle diameter exceeded 30 nm.

| [Amount of Z-PLLA30 Added] | [Particle Diameter] |
|---|---|
| 0 mol % | 20 nm |
| 15 mol % | 20 nm |
| 25 mol % | 21 nm |
| 50 mol % | 24 nm |
| 75 mol % | 27 nm |
| 100 mol % | 30 nm |
| 125 mol % | 33 nm |
| 150 mol % | 38 nm |

Figure 3:
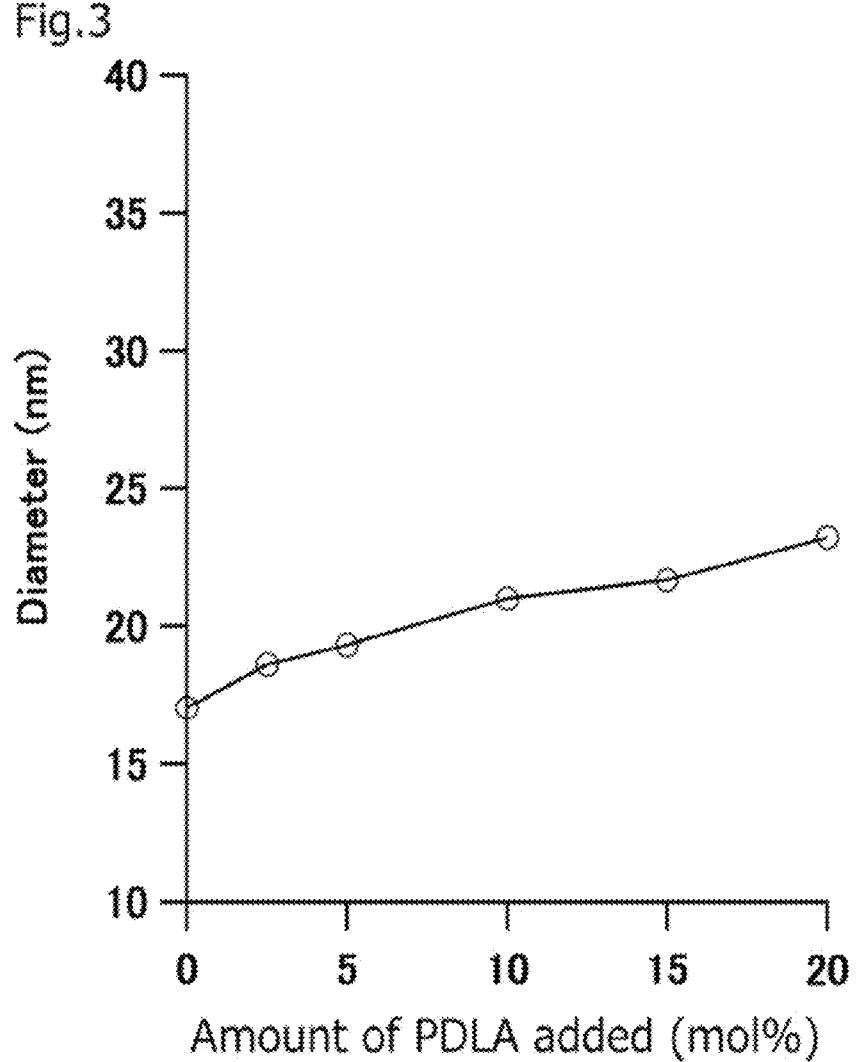
FIG. 3 is a graph showing changes in the particle diameter of a lactosome due to the addition amounts of poly-D-lactic acid (PDLA) in Experimental Example 2.

The amounts of the Z-poly-D-lactic acid (Z-PDLA30) added were 0, 2.5, 5, 10, 15, and 20 mol % with respect to the amount of the branched-type amphiphilic block polymer, PLLA30-(Psar23)3. The particle diameters of the obtained lactosomes are shown in FIG. 3. In FIG. 3, the vertical axis represents the particle diameter (Diameter (nm)), and the horizontal axis represents the amount of Z-PDLA30 added (mol %). Even when Z-PDLA30 having different stereochemistry from PLLA30-(Psar23) 3 was added up to 20 mol %, the particle diameter was increased only up to 23 nm as the amount of Z-PDLA30 added was increased. This revealed that the particle diameter is kept small.

| [Amount of Z-PDLA30 Added] | [Particle Diameter] |
|---|---|
| 0 mol % | 17 nm |
| 2.5 mol % | 18 nm |
| 5 mol % | 19 nm |
| 10 mol % | 21 nm |
| 15 mol % | 22 nm |
| 20 mol % | 23 nm |

Experimental Example 3

Evaluation of Disposition of Lactosome by Addition of ICG-Labeled Polylactic Acid Lactosome particles were obtained in the same manner as in Experimental Example 1 except that 1.5 mol % of each of the above-described ICG-labeled polylactic acids (ICG-PLLA, ICG-PDLA, ICG-PDLLA) with respect to the amount of the branched-type amphiphilic block polymer, PLLA30-(Psar23)3 was dissolved in chloroform together with PLLA30-(Psar23)3. The solvent of the thus obtained lactosome dispersion liquid was replaced with normal saline by gel filtration (PD-10 column, GE Healthcare). In this way, dispersion liquids of lactosome particles were prepared which were different in the stereochemistry of the ICG-labeled polylactic acid encapsulated in the lactosome. Each of the lactosomes had a particle diameter of 22 nm.

In-vivo fluorescent imaging of cancer-bearing mice (right lower limb, subcutaneous inoculation) was performed using the lactosome particles obtained in this Experimental Example and encapsulating the different ICG-labeled polylactic acids.

As animals, 7-week-old Balb/c nu/nu mice (CLEA) were used. The right lower limb of each of the mice was subcutaneously inoculated with $5 \times 10^5$ cells/0.02 mL of human pancreatic cancer cells (Suit2). At the time when the cancer tissue reached a size of 3 to 7 mm after growth for 2 weeks, the mice were subjected to the following imaging test.

The cancer-bearing mice were anesthetized with isoflurane and were administered with the lactosome particles encapsulating the different ICG-labeled polylactic acids (ICG-PLLA, ICG-PDLA, ICG-PDLLA) so that the concentration of ICG per one cancer-bearing mouse was 0.2 nmol, and the fluorescence intensity of ICG was observed with time. The images of the whole body of each of the mice were taken from five directions, that is, from all the directions of left abdomen, left side of the body, back, right side of the body, and right abdomen. The fluorescent dye was excited at 785 nm, and fluorescence at about 845 nm was measured with time.

Figure 4:
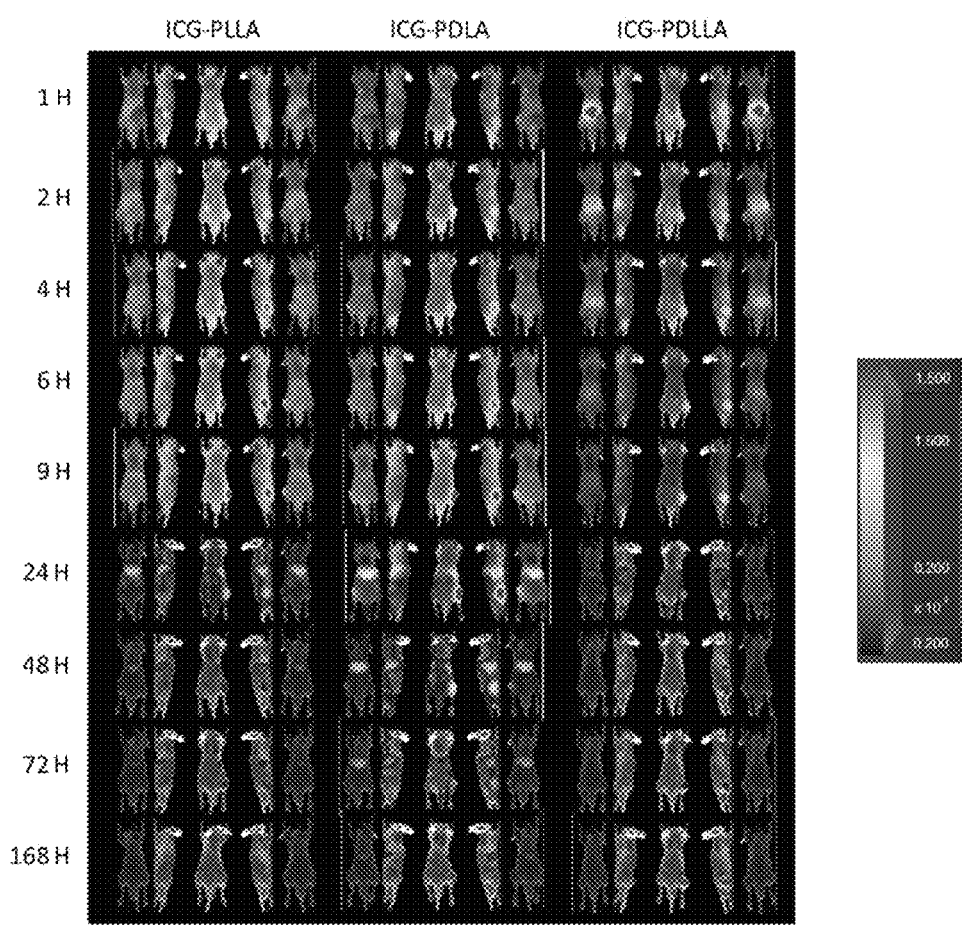
FIG. 4 shows the results of in-vivo fluorescent imaging of cancer-bearing mice using lactosome particles encapsulating different ICG-labeled polylactic acids (ICG-PLLA, ICG-PDLA, ICG-PDLLA) in Experimental Example 3.

The thus obtained images are shown in FIG. 4. The images in order from top to bottom show results measured after 1 hour to 168 hours from the administration of the ICG-labeled lactosome, and the images in order from left to right show results measured using the ICG-labeled lactosomes encapsulating ICG-PLLA, ICG-PDLA, and ICG-PDLLA, respectively in the lactosomes. In FIG. 4, a difference (variation) in fluorescence intensity is indicated by a difference in color tone.

Figure 5:
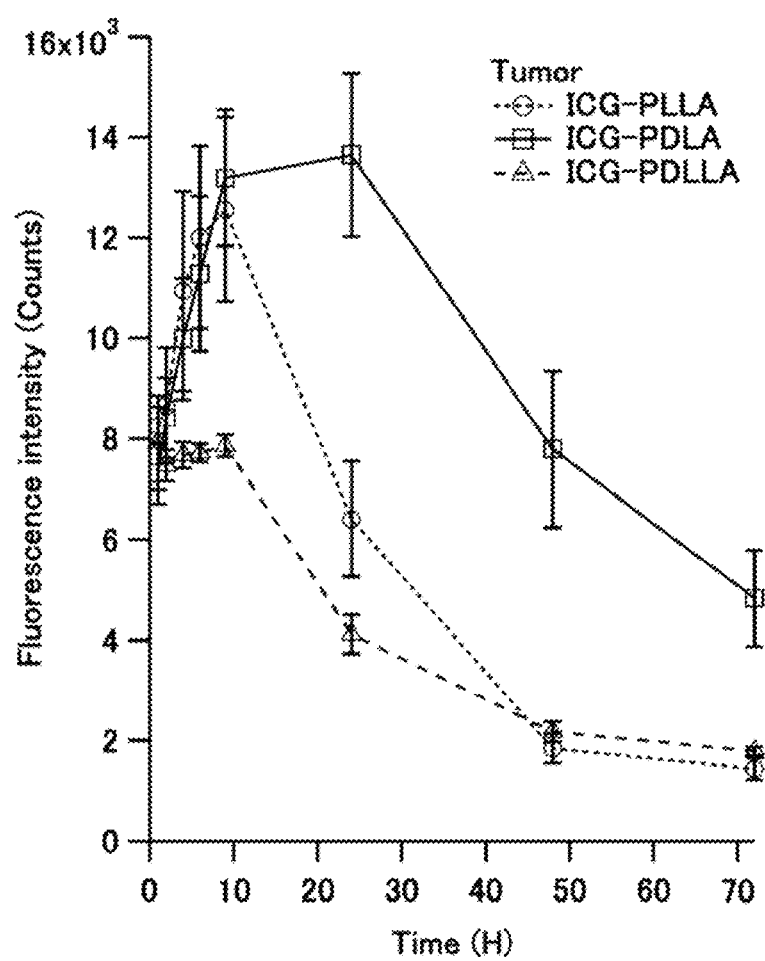
FIG. 5 is a graph showing changes in fluorescence intensity with time in tumor (Tumor) in the fluorescent imaging of cancer-bearing mice in Experimental Example 3.
Figure 6:
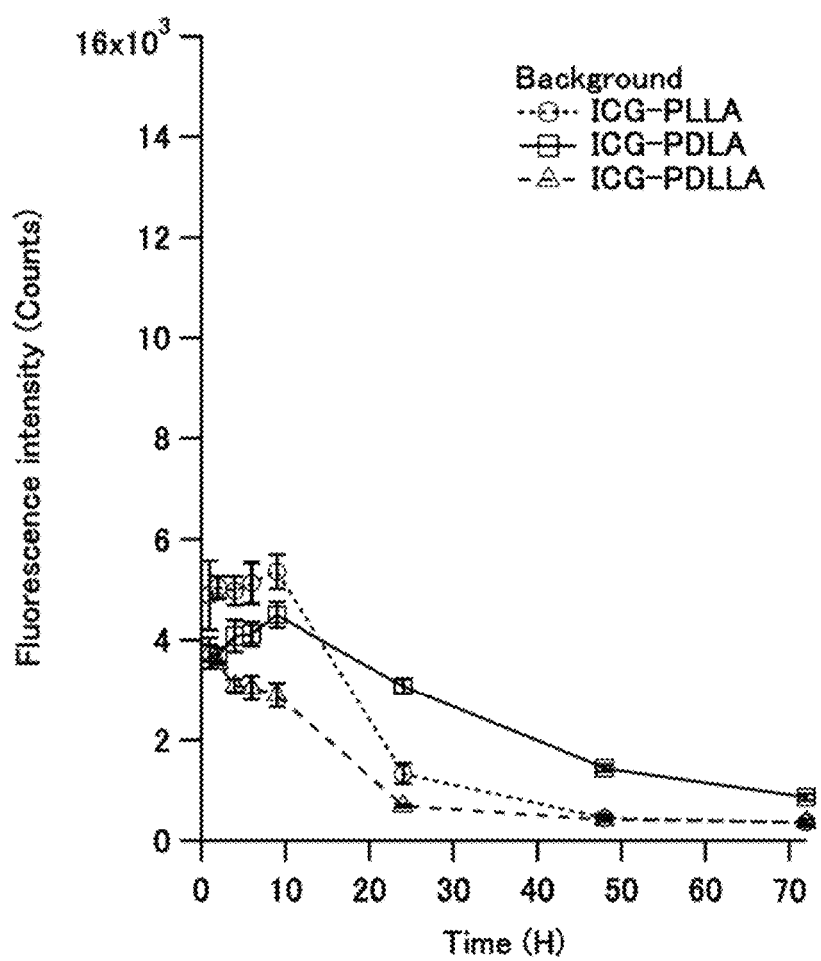
FIG. 6 is a graph showing changes in fluorescence intensity with time in back (Background) in the fluorescent imaging of cancer-bearing mice in Experimental Example 3.
Figure 7:
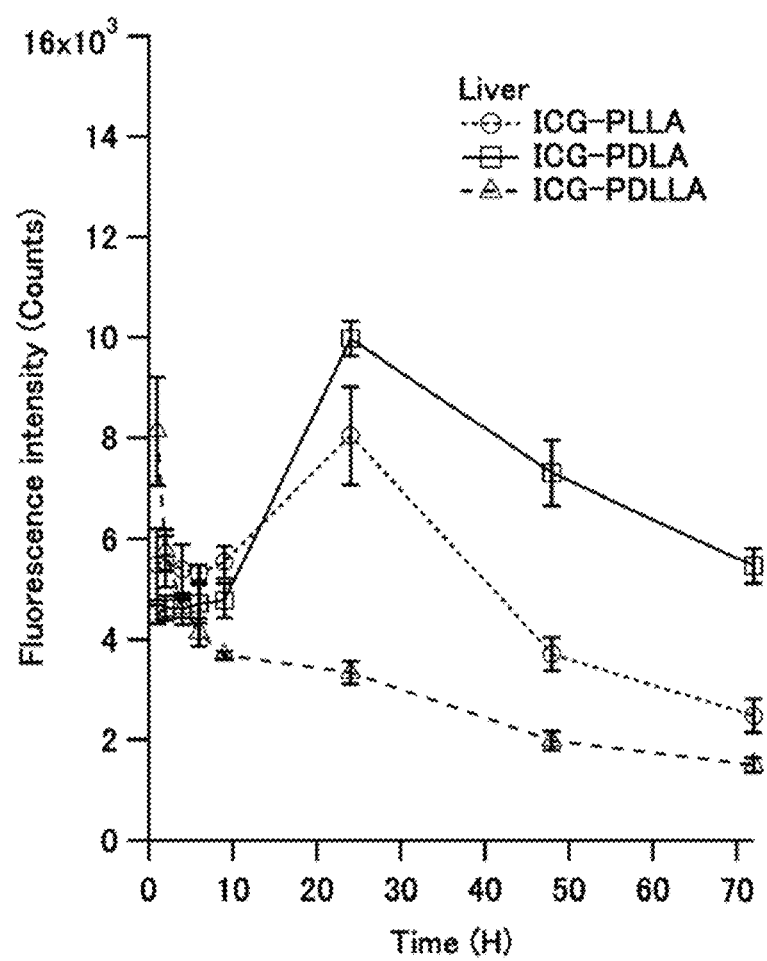
FIG. 7 is a graph showing changes in fluorescence intensity with time in liver (Liver) in the fluorescent imaging of cancer-bearing mice in Experimental Example 3.

As can be seen from the measurement results, accumulation of all the ICG-labeled lactosomes in the tumor in the right lower limb was observed. The analysis results of changes in fluorescence intensity (Fluorescence intensity) with time in tumor (Tumor), back (Background), and liver (Liver) are shown in FIGS. 5, 6, and 7. In each of FIGS. 5, 6, and 7, the vertical axis represents fluorescence intensity (Fluorescence intensity), and the horizontal axis represents time (Time (H)). When the ICG-labeled lactosome encapsulated ICG-PLLA or ICG-PDLLA, the peak of accumulation of the ICG-labeled lactosome in the tumor was observed after 9 hours from the administration, whereas when the ICG-labeled lactosome encapsulated ICG-PDLA, the peak of accumulation of the ICG-labeled lactosome in the tumor was observed after 24 hours from the administration. From the results, it is considered that when encapsulating ICG-PDLA, the ICG-labeled lactosome retained in the tumor for a longer time. Further, in the fluorescence intensity of background measured after 2 hours to 48 hours from the administration, the fluorescence intensity in the case where the ICG-labeled lactosome encapsulated ICG-PDLLA was lower than that in the case where the ICG-labeled lactosome encapsulated ICG-PLLA or ICG-PDLA. Similarly, in the fluorescence intensity in liver measured after 6 hours to 168 hours from the administration, the fluorescence intensity in the case where the ICG-labeled lactosome encapsulated ICG-PDLLA was low. From the results, it is considered that when encapsulating ICG-PDLLA, the ICG-labeled lactosome was more quickly excreted to the outside of the body. Therefore, the ICG-labeled lactosome encapsulating ICG-PDLLA is suitable for quicker imaging.

Figure 8:
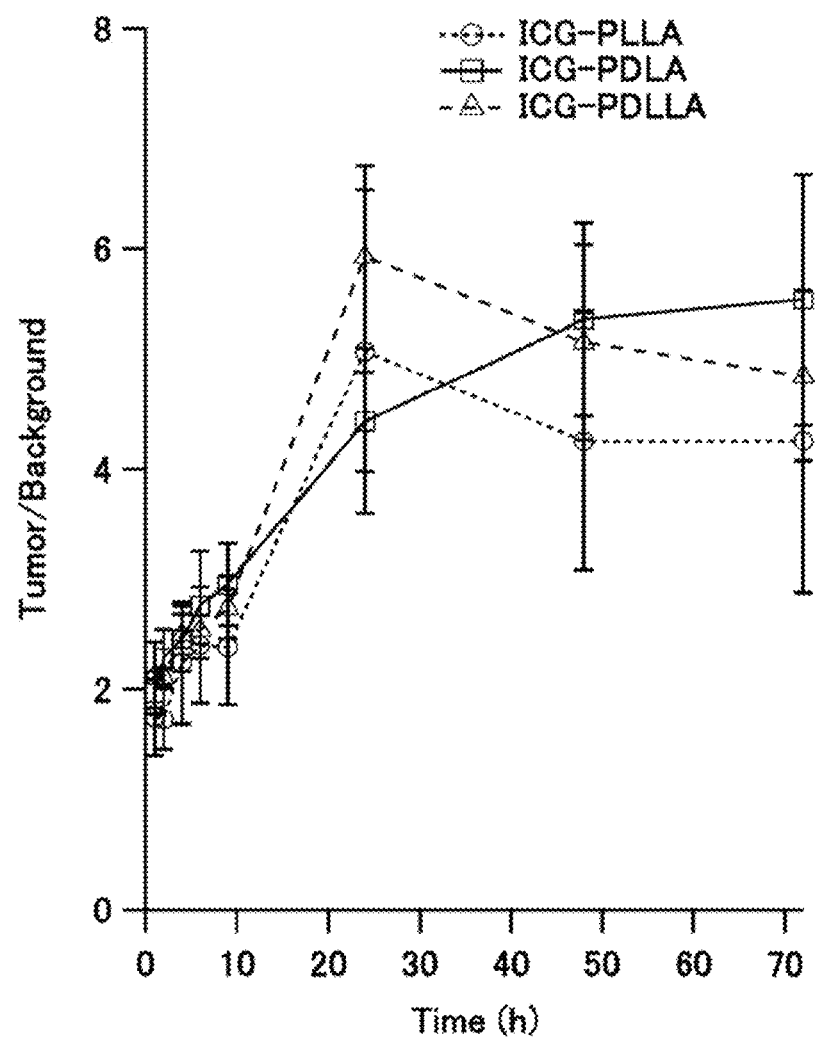
FIG. 8 is a graph showing the fluorescence intensity ratio (Tumor/Background) of tumor (Tumor) to back (Background) based on the analysis of the fluorescent imaging of cancer-bearing mice in Experimental Example 3.

FIG. 8 shows the analysis result of the fluorescence intensity ratio of tumor to background (Tumor/Background).

In FIG. 8, the vertical axis represents the fluorescence intensity ratio (Fluorescence intensity ratio of Tumor/Background), and the horizontal axis represents time (Time (H)). As can be seen from the results, the highest ratio of T/B after 24 hours from the administration of the ICG-labeled lactosome was 5.9, which was achieved when the ICG-labeled lactosome encapsulated ICG-PDLLA. Further, the highest ratio of T/B after 72 hours from the administration of the ICG-labeled lactosome was 5.5, which was achieved when the ICG-labeled lactosome encapsulated ICG-PDLA. That is, the T/B contrast after a long time from the administration was higher when the ICG-labeled lactosome encapsulated ICG-PDLA.

The invention claimed is:

1. A molecular assembly comprising:
    a branched-type amphiphilic block polymer A comprising a branched hydrophilic block comprising a polysarcosine and a hydrophobic block comprising a polylactic acid chain; and
    a functional substance F comprising a functional site and a polylactic acid chain, wherein
    the polylactic acid chain constituting the hydrophobic block of the amphiphilic block polymer A comprises L-lactic acid units, and the polylactic acid chain contained in the functional substance F comprises D-lactic acid units, or
    the polylactic acid chain constituting the hydrophobic block of the amphiphilic block polymer A comprises D-lactic acid units, and the polylactic acid chain contained in the functional substance F comprises L-lactic acid units, wherein the functional site of the functional substance F is a site selected from the group consisting of a signal agent and a drug.

2. The molecular assembly according to claim 1, wherein the hydrophilic block comprises 2 to 2.00 sarcosine units in total.

3. The molecular assembly according to claim 1, wherein the number of branches of the hydrophilic block is 3.

4. The molecular assembly according to claim 1, wherein the polylactic acid chain constituting the hydrophobic block comprises 10 to 400 lactic acid units.

5. The molecular assembly according to claim 1, wherein the hydrophobic block is not branched.

6. The molecular assembly according to claim 5, wherein the plurality of hydrophilic blocks extend as branches from one carbon atom in a molecular chain containing the polylactic acid chain of the hydrophobic block.

7. The molecular assembly according to claim 6, wherein the amphiphilic block polymer A has a structure represented by the following formula (I):

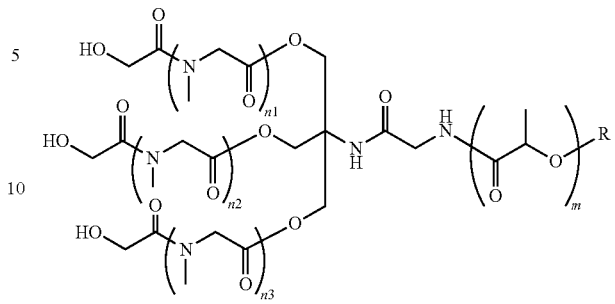

wherein n1, n2, and n3 represent numbers whose sum is 3 to 200, m represents a number of 15 to 60, and R represents a hydrogen atom or an organic group.

8. The molecular assembly according to claim 1, wherein in the amphiphilic block polymer A, a ratio of a total number of the sarcosine units contained in the hydrophilic block to a total number of the lactic acid units contained in the hydrophobic block is 0.05 or more and less than 1.8.

9. The molecular assembly according to claim 1, wherein the functional substance F is contained in an amount of 20 mol % or less with respect to the amphiphilic block polymer A.

10. The molecular assembly according to claim 1, whose particle diameter is 10 to 30 nm.

11. The molecular assembly according to claim 1, which is obtained by a preparation method comprising the steps of:
    preparing a solution, in a container, containing the branched-type amphiphilic block polymer A and the functional substance F in an organic solvent;
    removing the organic solvent from the solution to obtain a film comprising the branched-type amphiphilic block polymer A and the functional substance F on an inner wall of the container; and
    adding water or an aqueous solution into the container and performing ultrasonic treatment to convert the film into a molecular assembly, thereby obtaining a dispersion liquid of the molecular assembly.

12. The molecular assembly according to claim 1, which is obtained by a preparation method comprising the steps of:
    preparing a solution, in a container, containing the branched-type amphiphilic block polymer A and the functional substance F in an organic solvent;
    dispersing the solution into water or an aqueous solution; and
    removing the organic solvent.

13. A drug delivery system for a non-human animal comprising the molecular assembly according to claim 1.

* * * * *